(12) United States Patent
Geier et al.

(10) Patent No.: US 10,577,614 B2
(45) Date of Patent: Mar. 3, 2020

(54) **COMPACT AND OPTIMIZED METABOLIC PATHWAY DESIGN IN *PICHIA PASTORIS***

(71) Applicant: ACIB GmbH, Graz (AT)

(72) Inventors: Martina Geier, Graz (AT); Pia Fauland, Graz (AT); Anton Glieder, Hofstätten an der Raab (AT)

(73) Assignee: BISY GmbH, Hofstätten an der Raab (AT)

( * ) Notice: Subject to any disclaimer, the term of this patent is extended or adjusted under 35 U.S.C. 154(b) by 0 days.

(21) Appl. No.: 15/522,612

(22) PCT Filed: Oct. 28, 2015

(86) PCT No.: PCT/EP2015/075033
§ 371 (c)(1),
(2) Date: Apr. 27, 2017

(87) PCT Pub. No.: WO2016/066711
PCT Pub. Date: May 6, 2016

(65) Prior Publication Data
US 2017/0314031 A1    Nov. 2, 2017

(30) Foreign Application Priority Data
Oct. 28, 2014 (EP) .................................. 14190702

(51) Int. Cl.
| | |
|---|---|
| *C12N 15/81* | (2006.01) |
| *C12P 17/16* | (2006.01) |
| *C12P 21/00* | (2006.01) |
| *C12P 23/00* | (2006.01) |

(52) U.S. Cl.
CPC .......... *C12N 15/81* (2013.01); *C12P 17/165* (2013.01); *C12P 21/00* (2013.01); *C12P 23/00* (2013.01)

(58) Field of Classification Search
None
See application file for complete search history.

(56) References Cited

U.S. PATENT DOCUMENTS 9,822,357 B2 * 11/2017 Vogl .................. C12N 15/1086

| | | | |
|---|---|---|---|
| 2004/0265955 A1* | 12/2004 | Fang ...................... | C07K 16/00 435/69.1 |
| 2006/0228336 A1* | 10/2006 | Ko ...................... | A61K 48/0058 424/93.2 |
| 2007/0116690 A1* | 5/2007 | Yang .................. | A01K 67/0271 424/93.21 |

FOREIGN PATENT DOCUMENTS

EP    2862933 A2    4/2015

OTHER PUBLICATIONS

Arnau et al., "Current strategies for the use of affinity tags and tag removal for the purification of recombinant proteins" 48 Protein Expression and Purification 1-13 (2006).*
European Search Report for EP 14190702.2, dated Mar. 31, 2015.
International Search Report for PCT/EP2015/075033, dated Jan. 18, 2016.
Written Opinion of the International Search Authority for PCT/EP2015/075033, dated Jan. 18, 2016.
International Preliminary Report on Patentability for PCT/EP2016/075033, dated May 2, 2017.
Araya-Garay, JM et al., Appl. Microbiol. Biotechnol., 93: 2483-2492, 2012 (published online Dec. 9, 2011).
Beekwilder, J et al., J. Biotechnol., 192: 383-392, 2014.
De Felipe, P et al., J. Biol. Chem., 278(13): 11441-11448, 2003.
Donnelly, ML et al., J. Gen. Virol., 82: 1013-1025, 2001.
Gibson, D et al., Nat. Methods, 6(5): 343-345, 2009.
Hecht, K et al., FEMS Yeast Res., 2: 215-224, 2002.
Lin, Y-J et al., PLoS One, 8(3): e59099, 2013.
Lin-Cereghino, J et al., Biotechniques, 38(1): 44-48, 2005.
Naatsaari, L et al., PLoS One, 7(6): e39720, 2012.
Park, M et al., Appl. Microbiol. Biotechnol., 81: 43-49, 2008.
Radcliffe, PA et al., Gene Therapy, 11: 1673-1674, 2004.
Roongsawang, N et al., FEMS Yeast Res., 10: 909-916, 2010.
Ryan, MD et al., J. Gen. Virol., 72: 2727-2732, 1991.
Sun, Y-F et al., Appl. Microbiol. Biotechnol., 96: 1539-1550, 2012.
Szymczak, A et al., Nat. Biotechnol., 22(5): 589-594, 2004.
Unkles, S et al., Chem. Biol., 21: 502-508, 2014.
Wang, S et al., Appl. Microbiol. Biotechnol., 77: 891-899, 2007.
Weis, R et al., FEMS Yeast Res., 5: 179-189, 2004.
Zhu, T et al., Biotechnol. Lett. 31: 679-684, 2009.

* cited by examiner

*Primary Examiner* — Nancy J Leith
(74) *Attorney, Agent, or Firm* — Medler Ferro Woodhouse & Mills PLLC

(57) ABSTRACT

The present invention relates to an optimized metabolic pathway design in *P. pastoris*. In particular, to a recombinant polycistronic expression construct for stable expression of multiple genes of interest in a yeast cell, preferably in *P. pastoris*.

18 Claims, 21 Drawing Sheets

Specification includes a Sequence Listing.

a)                                    b)

Fig. 12A
Fig. 12B
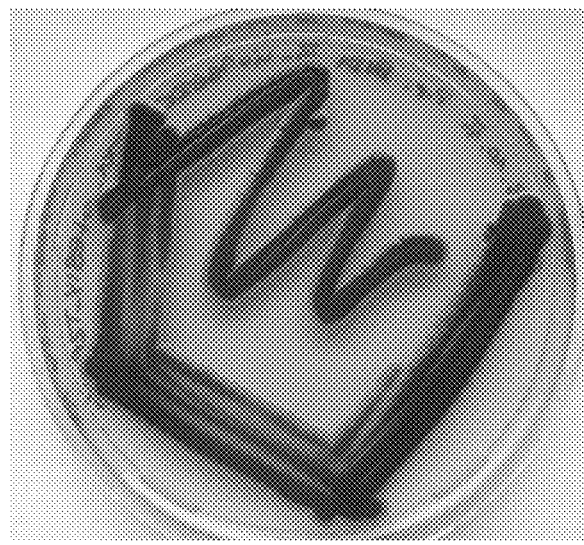
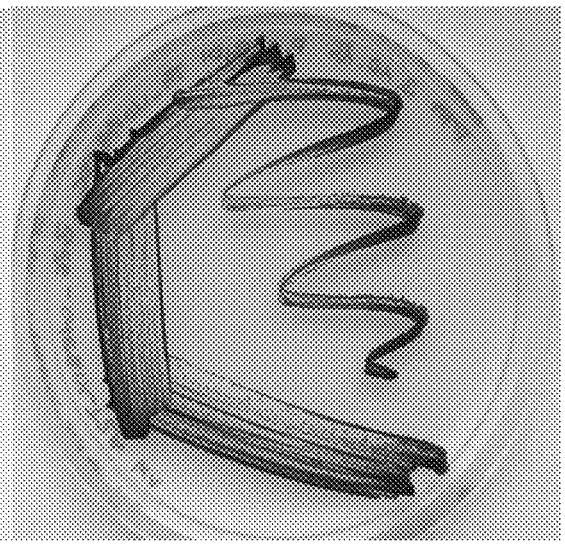

US 10,577,614 B2

COMPACT AND OPTIMIZED METABOLIC PATHWAY DESIGN IN *PICHIA PASTORIS*

FIELD OF THE INVENTION

The present invention relates to an optimized metabolic pathway design in *P. pastoris*. In particular, to a recombinant polycistronic expression construct for stable expression of multiple genes of interest in a yeast cell, preferably in *P. pastoris*.

BACKGROUND ART

Nowadays, an emerging challenge is not to produce single proteins only, but to implement whole pathways into microorganisms. Such engineered strains provide new opportunities in industrial processes e.g. for the production of valuable building blocks, derivatives of complex secondary metabolites or to improve cellular functions where multiple proteins are involved such as protein folding, secretion and resistance to environmental stress. For this purpose the genetic stability of production strains is of major importance.

Up to now, expressing three or more genes in *P. pastoris* is mainly achieved by employing the same regulatory elements. However, the repeated use of homologous sequences can result in recombination events and thus in genetic instability [1]. In addition, the transformation rates of microbial cells usually decrease with increasing the size of the expression constructs while technological difficulties and the costs for labor and materials increase with the size. However, most published engineered and synthetic pathways comprise sets of three to five additional genes which need to be coexpressed, while pathways of natural secondary metabolites are usually even longer.

One strategy to reduce the loss of genes by homologous recombination is the use of different promoter and terminator sequences for each individual gene of the pathway. Alternatively, the number of regulatory elements can be reduced by the expression of multiple genes from a single, polycistronic transcript. While this is simple to achieve in prokaryotes, this is more difficult for eukaryotes. However, such a coordinate expression can be achieved by employing self-processing 2A sequences [2]. 2A sequences are short peptides (up to 20 amino acids) originating from viral polyproteins. They are supposed to cause a ribosome "skip" resulting in the cleavage of the polycistronic transcript between the Gly and the Pro at the C-terminus of the 2A sequence [3]. 2A sequences have already been successfully employed for polycistronic expression in various hosts including the yeast *S. cerevisiae* up to three proteins were produced employing this strategy [4, 5] and also *P. pastoris* (*Komagattaella phaffi*) where 2 proteins have been coexpressed from the same vector using 2A technology [6-8]. Four genes have been coexpressed. To avoid nonstoichiometric expression of multiple proteins as known for genes coupled by IRES sequences Szymczak et al expressed 4 CD3 proteins linked by 2A sequences and showed stoichiometric production of two fluorescent proteins in multiple cell types [9].

Heterologous gene expression of up to three gene copies in a mushroom, Flammulina velutipes using polycistronic vectors was described [16] and the use of 2A peptides for expression of up to four proteins were further described by Radcliffe and Mitrophanous [17]. Felipe et al. showed that 2A peptides worked in the yeast *Saccharomyces cerevisiae*. [18], Hecht et al [19] described poycistronic gene expression in yeast.

SUMMARY OF INVENTION

It is the objective of the present invention to provide a recombinant polycistronic expression construct for optimized expression of multiple genes in a yeast cell, consecutively comprising in the 5' to 3' orientation a promoter operable in said yeast cell, at least five genes of interest which are separated by 2A sequences from each other and a termination signal.

It is a further object of the invention to provide a method for optimized expression of multi-enzyme pathways in the methylotrophic yeast *Pichia pastoris*.

Therefore, another object of this invention is to obtain technologies for the stable multi-gene construction going beyond the current limits of the state of the art.

BRIEF DESCRIPTION OF DRAWINGS

FIG. 12: *P. pastoris* strains harboring the β-carotene and violacein pathway on expression constructs based on 2A sequences in combination with a bidirectional constitutive (panel A) or inducible promoter (panel B).

FIG. 16 B: Plasmid map of the polycistronic expression construct coding for the β-carotene and the violacein biosynthesis pathway in different order.

DESCRIPTION OF EMBODIMENTS

Figure 1:
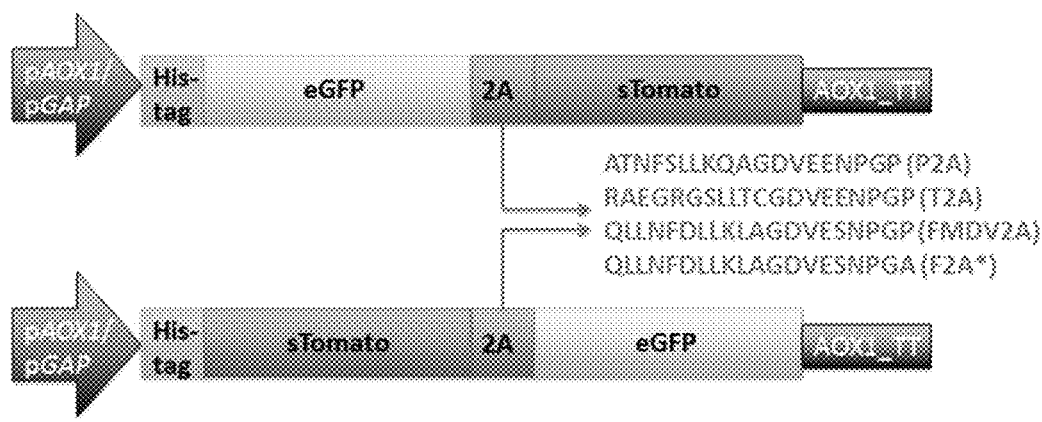
FIG. 1: Schematic representation of the expression construct for testing the 2A activity in *P. pastoris*. The 2A sequence was variable—four different sequences were tested (P2A, T2A, FMDV2A, F2A*).
Figure 2A:
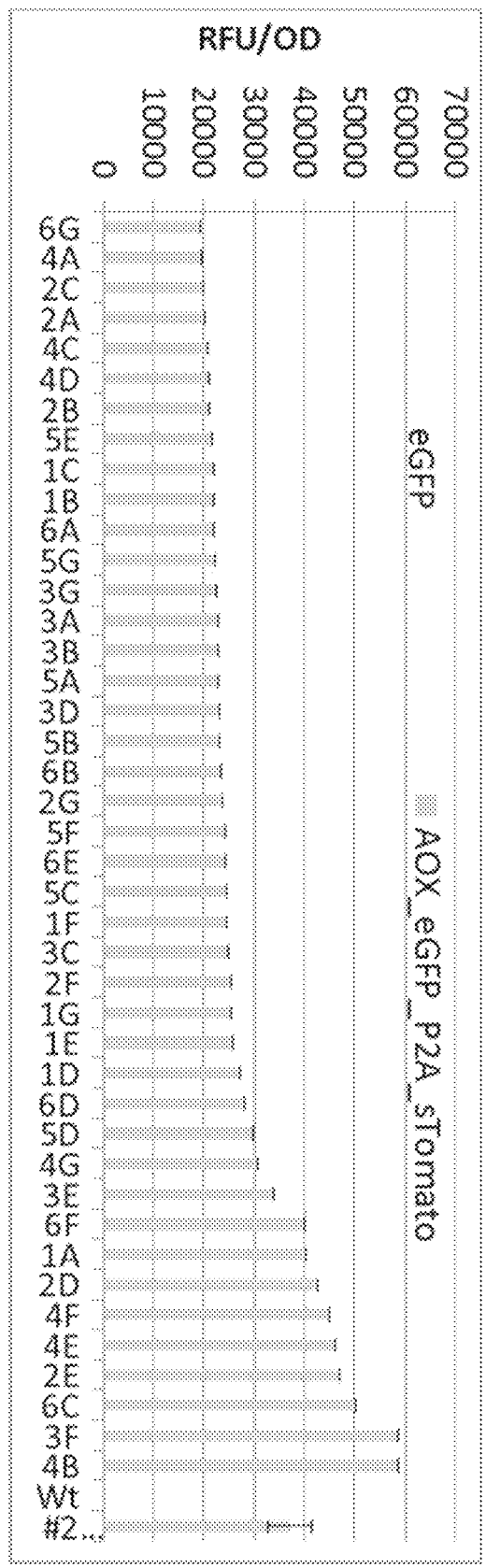
FIG. 2: eGFP and sTomato fluorescence levels obtained by coordinate expression based on 2A sequences. Exemplarily, the screening results of the construct pPp_T4_S_eGFP_P2A_sTomato (panel A and C) and pPp_T4_S_sTomato_P2A_eGFP (panel B and D) are shown. *P. pastoris* CBS 7435 was used as negative control, strain #243 expressing eGFP and sTomato served as positive control.
Figure 2B:
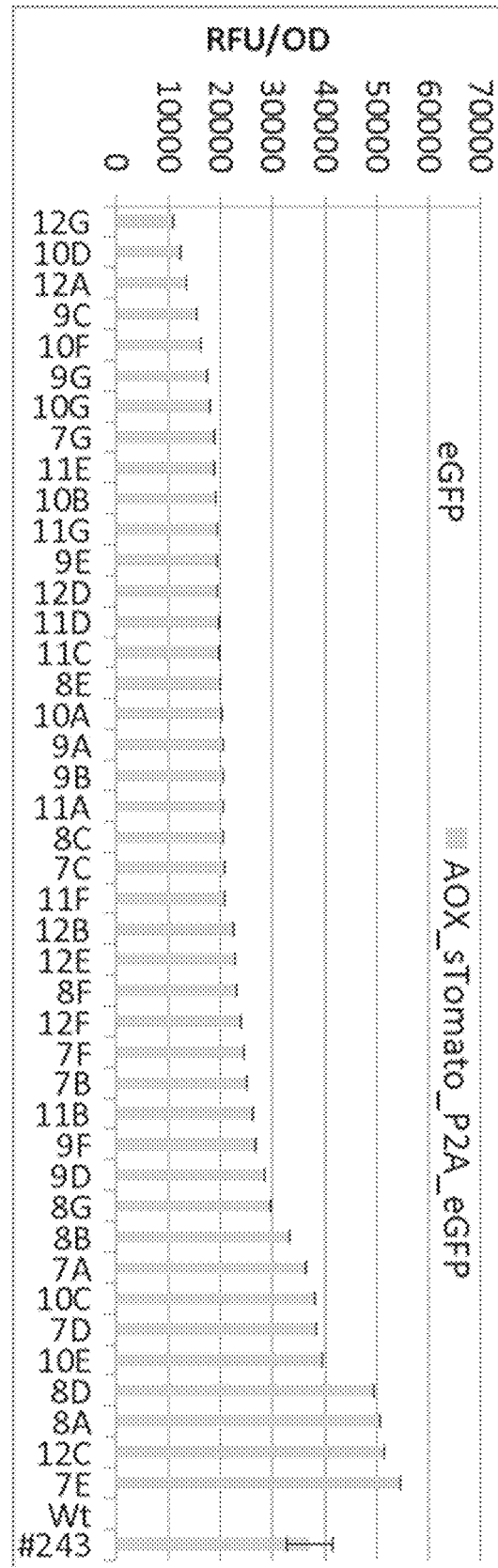
Figure 2C:
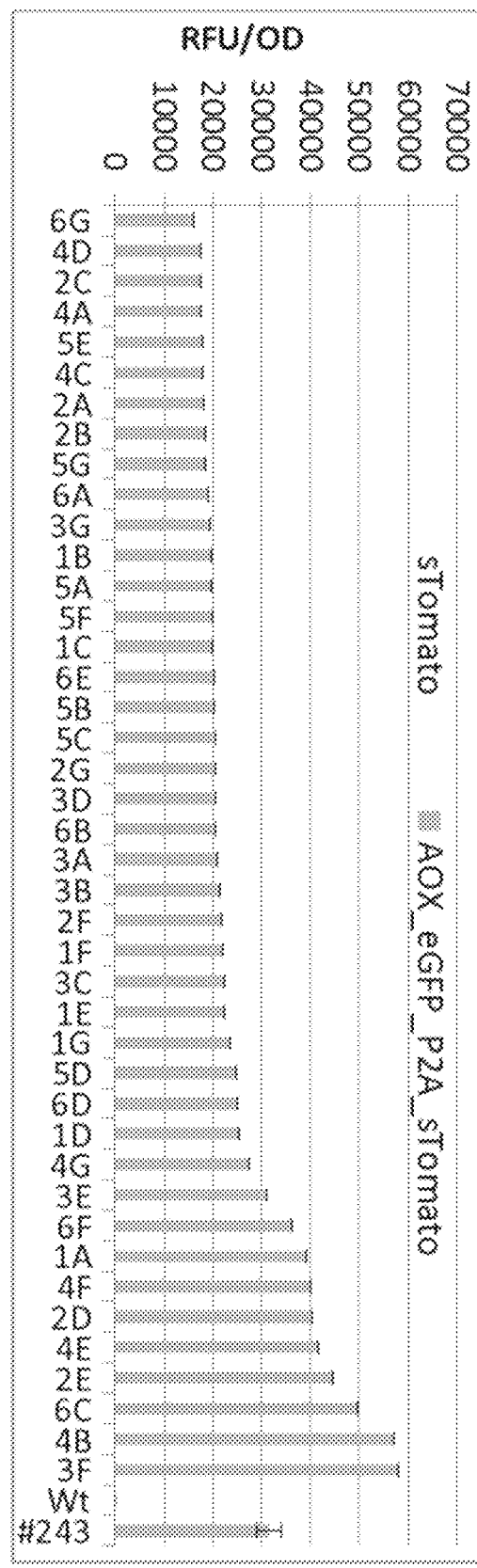
Figure 2D:
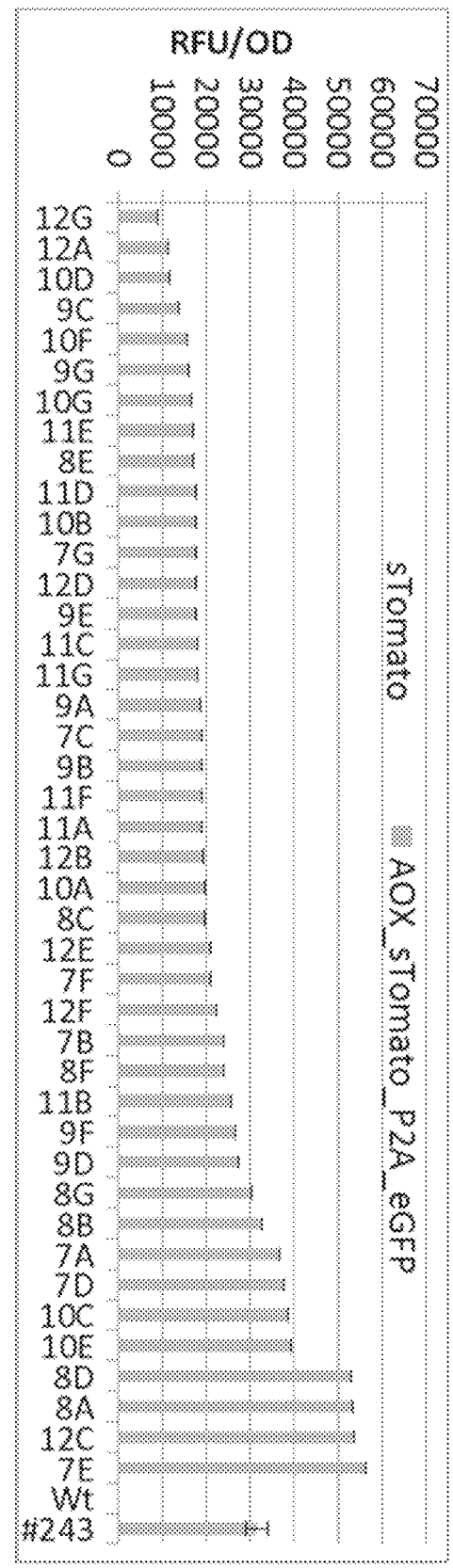

In a first aspect, the invention relates to a recombinant polycistronic expression construct for stable expression of multiple genes in a yeast cell, consecutively comprising in the 5' to 3' orientation, a promoter operable in said yeast cell, at least five genes of interest which are separated by 2A sequences, and a termination signal. Such construct can be made in vitro as a whole construct including all those elements or include just parts of the final construct to complement existing sequences of the cell.

The 2A fusion strategy avoids the multiple use of promoters and terminators which often cause instabilities of the pathways due to homologous recombination. In addition, internal promoters may suffer from downregulation and smaller expression constructs are needed to code for a whole metabolic pathway including the necessary regulatory sequences for transcription and translation.

Employing a polycistronic expression constructed based on 2A sequences has many advantages in comparison to coexpression constructs harboring a set of regulatory elements per gene. The pathway can be easily assembled via the 2A sequences employing convention cloning, e.g. Gibson cloning, in vivo recombination or overlap-extension PCR. In addition, the corresponding polycistronic constructs are significantly reduced in size, e.g. the 2A sequences consist of about 60 bp whereas one promoter/terminator pair comprises at least 1,000 bp. Thus, the inventive polycistronic construct can be transformed more efficiently into the respective host cells and also allows the construction of longer pathways by simple technologies. The repetitive use of identical promoter and terminator sequences was shown to cause genetic instability due to homologous recombination events. This problem can be circumvented by employing diverse regulatory elements, but requires the availability of those. Thus, use of 2A sequences facilitates the stable and compact pathway design for yeast cell, specifically for *P. pastoris* cell.

In addition transformation of host cells is more efficient since efficiency decreases with the size of the expression cassette. Thus, this technology is also a key technology to enable coexpression of genes in signal cascades, enzyme cascades and whole metabolic pathways for industrial biotechnology, cell engineering and gene therapies depending on multiple gene pathways. The small and compact design also facilitates direct laboratory evolution experiments of whole metabolic pathways.

The present invention relates to exploit this system for the expression of balanced long biosynthetic pathways. The inventive expression construct is more compact in comparison to state of the art expression strategies. More importantly, the corresponding *P. pastoris* strains show a stable expression of a physiologically problematic pathway where the four gene pathway established in *P. pastoris* seemed to be even more problematic than the three gene pathway expressed in *S. cerevisiae* for β-carotene production.

A further aspect of the invention is a polycistronic expression construct as described above, wherein at least six, seven, eight, nine, ten, eleven and up to twenty genes of interest are separated by 2A sequences.

Positioning individual genes on different positions within long polycistronic constructs enables fine tune pathway expression as an attractive alternative to transcriptional regulation by different individual promoters. The short DNA sequences coding for 2A peptide sequences provide an opportunity to serve as universal linkers for random combinatorial assembly of the individual coding sequences to optimize the order for optimized and balanced expression of individual pathway components. Thus, 2A sequences can also be exploited to generate shuffled libraries containing the pathway genes in variable order and copies or functional homologs of individual pathway proteins.

Thus, a further aspect of the invention is a polycistronic expression construct as described above, wherein the alignment of the at least five genes is optimized.

A further aspect of the invention is a polycistronic expression construct, wherein said promoter is a bidirectional promoter.

Bidirectional promoters provide divergent expression in opposing (forward and reverse) orientations. Currently available bidirectional expression vectors rely on a bidirectional promoter flanked by two multiple cloning sites to clone in the genes to be expressed. Novel bidirectional promoters are described in EP14175932.4.

A further aspect of the invention is a recombinant polycistronic expression construct for stable expression of multiple genes in a yeast cell, consecutively comprising in the 5' to 3' orientation a terminator, at least two or more genes of interest which are separated by 2A sequences, a bidirectional promoter, at least two or more genes of interest which are separated by 2A sequences, and a terminator.

A further aspect of the invention is the polycistronic expression construct as described above, wherein at least four genes of interest are separated by 2A sequences.

A further aspect of the invention is the polycistronic expression construct as described above, further comprising a His-tag encoding sequence inserted between the promoter and the adjacent gene of interest.

Several viruses use 2A peptides, or 2A-like sequences, to mediate co-translational production of individual polypeptide chains from a single transcript. These include members of the Picorna viridae virus family, such as foot-and-mouth disease virus (FMDV) and equine rhinitis A virus (ERAV) and other viruses such as the porcine teschovirus-1 and the insect virus Thosea asigna virus (TaV). In such viruses, multiple proteins are derived from a large polyprotein encoded by a single open reading frame. The 2A peptide mediates the co-translational individual production of these polyproteins by a ribosome skipping effect at a single site that forms the junction between the virus capsid and replication polyprotein domains.

The 2A sequences are relatively short peptides (of the order of 20 amino acids long, depending on the virus of origin) containing the consensus motif -Asn-Pro-Gly-Pro. They were originally thought to mediate the autocatalytic proteolysis of the large polyprotein, but are now understood to act co-translationally, by preventing the formation of a normal peptide bond between the glycine and last proline, resulting in the ribosome skipping to the next codon, and the nascent peptide cleaving between the Gly and Pro [3]. 2A sequences have already been successfully employed for polycistronic expression in various hosts including the yeast *S. cerevisiae* up to three proteins were produced employing this strategy [4, 5].

Thus a further aspect of the invention is the polycistronic expression construct as described above, wherein the 2A sequences are derived from porcine teschovirus-1, Thosea asigna virus, foot-and-mouth-disease virus, and equine rhinitis A virus (ERAV).

A further aspect of the invention is the polycistronic expression construct as described above, wherein the 2A sequences comprise SEQ ID Nos.1-9.

A further aspect of the invention is that the DNA sequences coding for the 2A linker peptides are codon optimized to avoid homologous recombination effects in the cell.

A further aspect of the invention is the polycistronic expression construct as described above, wherein the 2A sequences are encoding a polypeptide of SEQ ID No.11-13.

A further aspect of the invention is the polycistronic expression construct as described above, wherein the 2A sequences are of identical or different sequences. Specifically, said sequences can be of SEQ ID Nos. 1 to 10, wherein any order and number of sequences may be applicable. Specifically each of the genes of interest is separated from the following one by SEQ ID No. 1, followed by SEQ ID No. 2. SEQ ID No. 3, SEQ ID No. 4, SEQ ID No. 5, SEQ ID No. 6, SEQ ID No. 7, SEQ ID No. 8, SEQ ID No. 9 and/or SEQ ID No. 10.

Yet another aspect of the invention is a method for producing a transgenic yeast cell, wherein said yeast cell is transformed with the polycistronic expression construct as described above.

Specifically, the yeast cell is a *P. pastoris* cell.

Biosynthesis is a multi-step, enzyme-catalyzed process where substrates are converted into more complex products. In biosynthesis, simple compounds are modified, converted into other compounds, or joined together to form macromolecules. This process often consists of metabolic pathways. Some of these biosynthetic pathways are located within a single cellular organelle, while others involve enzymes that are located within multiple cellular organelles and substrate/product pumps to detoxify the cell. Biosynthetic pathways have been elucidated for many common molecules such as for example terpenoids, steroids, carotenoids, alkaloids, fatty acids, amino acids, nucleotides and also macromolecules such as proteins, fat & waxes and sugar polymers.

Implementing natural and/or synthetic pathways into microorganisms provide new opportunities for the production of fine chemicals, building blocks and pharmaceutical compounds and complex biological mechanisms such as resistance to environmental stress and protein folding and targeting. Genetic stability of the production strains is a major requirement for their use in industrial processes. This gets an even increasing challenge in case of multi enzyme pathways in eukaryotic cells where engineered pathways so far contain multiple copies of the same promoter and terminator sequences to realize simultaneous overexpression of several genes under the same constitutive or inducible cultivation conditions. In addition the limitations for plasmid and expression cassettes construction are reached. Therefore, the current invention provides innovative tools and methods for the generation of stable eukaryotic cells expression multi-enzyme pathways employing compact polycistronic pathway design as described above.

A further aspect of the invention is a method of producing multiple polypeptides in a yeast cell comprising the steps of transforming the yeast cell with an expression construct as described above, expressing the construct, culturing the yeast cell under conditions sufficient to express the polypeptides of interest and isolating the polypeptides of interest.

Yet another aspect of the invention is a method for producing a compound comprising culturing a yeast cell comprising a polycistronic expression construct as described above under conditions such that the compound is produced.

A further aspect of the invention is a yeast cell containing a polycistronic expression construct as described above.

Specifically the yeast cell is a *P. pastoris* cell.

Therefore, the present invention focuses on the use of 2A sequences for pathway generation in *P. pastoris*.

As used therein the term "optimized" refers to an improved expression process through positioning individual genes on different positions within the polycistronic expression constructs, therefore having a significant effect on the pathway efficiency.

As used therein the term "gene of interest" means any nucleotide sequence, e.g. an open reading frame, capable of expressing a polypeptide or peptide. Preferably, the genes are protein-encoding sequences or parts of fragments thereof encoding enzymes or proteins of therapeutic or industrial applications. In the following the term "polypeptides" shall include peptides of interest having preferably at least three amino acids. The polypeptides of interest preferably are selected, but not limited to enzymes, specifically enzymes or protein catalysts triggering biosynthetic pathways including complex biological processes such as protein folding and environmental stress resistance, members of the immunoglobulin superfamily, such as antibodies and antibody domains or fragments, cytokines, vaccine antigens, growth factors and other peptides of interest.

Enzymatic catalysts are suitably used in many industrial processes because of their high selectivity. Preferred enzymes include proteolytic enzymes, carotene biosynthetic proteins, subtilisins; cellulolytic enzymes, such as cell-wall loosening enzymes, endoglucanases, amylosucrases, aldolases, sugar kinases, -transferases, glykosidases, cellulase, endoglucanase, amylase, xylanase, glucose dehydrogenase and beta-glucosidase, laccases; lipases, esterases, monooxygenases such as cytochromes P450, transaminases, oxidases, oxygenases and peroxygenases, methyltransferases, reductases, enzymes forming C—C bonds such as lyases and ligases as used in the synthesis of fine chemicals, agrochemicals and pharmaceuticals; etc.

As used herein, the term "transformation" means an overall action of introducing a gene into the host cell for its expression in the host cell. In this regard, the promoter and the gene are polynucleotides, including DNA and RNA. As long as the gene can be introduced in the host cell and expressed therein, any type of the gene can be used. For example, the expression construct of the invention can be introduced into the host cell in a form of an expression cassette which is a polynucleotide construct including optional further elements for expressing the gene. The expression cassette may further include a promoter which is operably linked to a further gene, a transcription termination signal, and consensus sequences for translation such as Kozak consensus sequence, and a translation termination signal. The expression cassette may be a form of an expression vector capable of self-replication, specifically it may be a plasmid, more specifically comprising additional selection and amplification markers as known in the art. The gene also may be introduced into the host cell by itself or in the inventive polynucleotide construct to be operably linked to the sequence necessary for expression in the host cell. The polycistronic multi gene construct may also be introduced into the cell without any additional promoter or terminator for example to be specifically integrated into an existing DNA locus by genome engineering methods such as CRISPR/Cas.

"Transformation" also refers to the transfer of a nucleic acid molecule into a host organism, resulting in genetically stable inheritance. The nucleic acid molecule may be a plasmid that replicates autonomously, for example, or, it may integrate into the genome or other DNA loci of the host organism. Host organisms containing the transformed nucleic acid fragments are referred to as "transgenic" or "recombinant" or "transformed" organisms.

The terms "vector" and "cassette" refer to an extra chromosomal element often carrying genes that are not part of the central metabolism of the cell, and usually in the form of circular double-stranded DNA fragments. Such elements may be autonomously replicating sequences, genome integrating sequences, phage or nucleotide sequences, linear or circular, of a single- or double-stranded DNA or RNA, derived from any source.

"Expression cassette" refers to a specific vector containing a foreign gene and having elements in addition to the foreign gene that allow for enhanced expression of that gene in a foreign host.

Vectors or DNA cassettes useful for the transformation of host cells are well known in the art. The specific choice of sequences present in the construct is dependent upon the desired expression products, the nature of the host cell, and the proposed means of separating transformed cells versus non-transformed cells. Typically, however, the vector or cassette contains sequences directing transcription and translation of the relevant gene(s), a selectable marker and sequences allowing autonomous replication or chromosomal integration. Most suitable vectors comprise a region 5' of the gene that controls transcriptional initiation (e.g., a promoter) and a region 3' of the DNA fragment that controls transcriptional termination (i.e., a terminator). It is most preferred when both control regions are derived from genes from the transformed host cell, although it is to be understood that such control regions need not be derived from the genes native to the specific species chosen as a production host.

The promoter sequences as used in the present invention may be any promoter sequences known in the art, which may be selected in accordance with the respective genes of interest to be expressed in the inventive expression constructs. Specifically it can be an AOX, DAS1, DAS2, CAT, TEF1, ADH, CUP1, ILV5 or GAP promoter and other known monodirectional yeast promoters or bidirectional promoters as described by patent application EP14175932.4.

The termination signals or terminator as used in the present invention may be any terminator signals known in the art, which may be selected according to the respective genes of interest. Specifically said terminator signals are AOX_TT, DAS_TT, CYC_TT, FBP1_TT, PXR1_TT, ADH2_TT, FBA2_TT, GCW14_TT, GAP_TT, TEF1_TT, FLD1_TT, CAT1_TT, FDH1_TT, TPI1_T, TAL2_TT and further known yeast terminators.

In a specific embodiment the genes of interest lack their own promoter and termination sequences, specifically said sequences are deleted from the respective genes and are replaced by one single promoter at the 5' end of the complete expression construct and by one single termination signal introduced at the 3 end of the expression construct or replaced by existing alternative promoter or terminator elements at the integration locus.

In a further specific embodiment different sequences with different capacity to form separate proteins of polycistronic constructs may be used.

A further embodiment relate to different arrangements of open reading frames to adjust the optimal expression level of the individual components of the multi protein construct and the ratio of fusion proteins compared to individual polypeptides.

Another specific embodiment relates to the order of the genes on the construct. It is advantageous when the gene or combination of several pathway genes where most of the translated product needed for an optimized well balanced pathway is located at the front of the construct. If these genes are located at suboptimal positions on the polycistronic construct it is possible that intermediates rather than products pile up.

In another embodiment sequences coupled by 2A peptides contain cleavable protein fusion partners in order to facilitate protein targeting to subcellular structures and to produce desired unmodified terminal sequences.

EXAMPLES

The examples which follow are set forth to aid in the understanding of the invention but are not intended to, and should not be construed to limit the scope of the invention in any way. The examples do not include detailed descriptions of conventional methods, e.g., cloning, transfection, and basic aspects of methods for overexpressing proteins in microbial host cells. Such methods are well known to those of ordinary skill in the art.

Material and Methods

Unless stated otherwise, all chemicals were obtained from Sigma-Aldrich (Steinheim, Germany) or Carl-Roth (Karlsruhe, Germany) with the highest purity available. Zeocin™ was obtained from InvivoGen (San Diego, Calif., USA). Phusion® High Fidelity Polymerase for DNA amplification and further DNA modifying enzymes were purchased from Thermo Fisher Scientific Inc. (Waltham, Mass., USA) or New England Biolabs (Ipswich, Mass., USA). *E. coli* Top10 (Invitrogen, Carlsbad, USA) was used for all cloning steps and plasmid propagation. The *P. pastoris* strain CBS7435 as well as the plasmids pPp_T4_S and pPp_T4_GAP_S were obtained from the *Pichia* pool of TU Graz [10].

Plasmid and Strain Generation

All expression constructs generated during this study are summarized in Table 2. Overlap-extension PCR as well as Gibson cloning [11] were employed for expression construct assembly. Primer sequences, 2A sequences as well as the corresponding plasmid maps are provided in the appendix.

TABLE 1

Expression constructs assembled during the present study.

| Expression construct | Remarks |
|---|---|
| pPp_T4_S_eGFP_T2A_sTomato | Construct also available with $P_{GAP}$ |
| pPp_T4_S_sTomato_T2A_eGFP | Construct also available with $P_{GAP}$ |
| pPp_T4_S_eGFP_P2A_sTomato | Construct also available with $P_{GAP}$ |
| pPp_T4_S_sTomato_P2A_eGFP | Construct also available with $P_{GAP}$ |
| pPp_T4_S_eGFP_F2A_sTomato | Construct also available with $P_{GAP}$ |
| pPp_T4_S_sTomato_F2A_eGFP | Construct also available with $P_{GAP}$ |
| pPp_T4_S_eGFP_FMDV2A_sTomato | Construct also available with $P_{GAP}$; in addition constructs harboring the CDS of sTomato with a start codon |
| pPp_T4_S_sTomato_FMDV2A_eGFP | Construct also available with $P_{GAP}$ |
| pPp_T4_S_crtEBIY, T2A | Construct also available with $P_{GAP}$ |
| pPp_T4_S_crtEBIY, T2A_P2A | Construct also available with $P_{GAP}$ |
| pPp_T4_S_vioCBEDA, T2A | Construct also available with $P_{GAP}$ |
| pPp_T4_S_crtEBIY_vioCBEDA, T2A | Construct also available with $P_{GAP}$ |
| pPp_T4_S_vioABEDC_crtEBIY, T2A | Construct also available with $P_{GAP}$ |
| pPp_T4_S_vioCBEDA_pHTX1_crtEBIY | Combination with bidirectional promoter |
| pPp_T4_S_vioCBEDA_pBZ6_crtEBIY | Combination with bidirectional promoter |

All constructs were linearized and used to *P. pastoris* CBS7435 according to the condensed protocol by Lin-Cereghino et al. [12]. Transformants were selected on YPD agar plates containing 100 mg/L Zeocin™.

TABLE 2

Nucleotide sequences of the 2A sequences used in the present study.

| Identifier | Nucleotide sequence |
|---|---|
| T2A1 | AGA GCT GAG GGT AGA GGT TCT TTG CTT ACT TGC GGT GAC GTT GAG GAA AAC CCA GGT CCA (SEQ ID NO: 1) |
| T2A2 | CGT GCC GAA GGA CGT GGA TCC CTT TTG ACC TGC GGA GAT GTC GAA GAG AAT CCT GGA CCT (SEQ ID NO: 2) |
| T2A3 | AGA GCA GAA GGT CGT GGC TCA TTG CTG ACT TGT GGC GAC GTG GAG GAA AAT CCC GGA CCA (SEQ ID NO: 3) |

TABLE 2-continued

Nucleotide sequences of the 2A sequences used in the present study.

| Identifier | Nucleotide sequence |
|---|---|
| T2A4 | CGT GCA GAG GGC CGT GGT TCC TTA CTT ACC TGC GGT GAT GTG AAA GAA AAT CCA GGA CCC (SEQ ID NO: 4) |
| T2A5 | CGT GCC GAG GGT AGG GGA TCA CTT CTT ACA TGT GGA GAC GTC GAG GAG AAC CCT GGT CCA (SEQ ID NO: 5) |
| T2A6 | AGA GCT GAA GGA AGG GGT TCC CTG TTA ACG TGT GGC GAT GTT GAA GAG AAC CCC GGT CCT (SEQ ID NO: 6) |
| T2A7 | AGG GCA GAA GGC AGA GGA TCT CTG TTG ACT TGT GGT GAT GTA GAG GAG AAT CCC GGC CCA (SEQ ID NO: 7) |
| T2A8 | AGG GCG GAG GGG AGA GGC TCT CTT TTA ACT TGT GGA GAT GTG GAA GAG AAC CCA GGC CCT (SEQ ID NO: 8) |
| P2A | GCT ACT AAC TTC TCT TTG CTT AAG CAA GCT GGT GAC GTT GAG GAA AAC CCA GGT CCA (SEQ ID NO: 9) |
| FMDV2A | CAA TTG CTT AAC TTC GAC TTA TTG AAG CTT GCT GGT GAC GTT GAG TCT AAC CCA GGT CCA (SEQ ID NO: 10) |

TABLE 3

Primers used for the assembly of polycistronic expression constructs coding for eGFP and sTomato.

| # | Name | Sequence (5'→3') |
|---|---|---|
| C337 | eGFP_EcoRI_fwd | AAA TGA ATT CCG AAA CGA TGG CTA GCA AAG GAG AAG AAC TTT TCA CTG (SEQ ID NO: 15) |
| C338 | eGFP_FMDV2A_rev | TGG ACC TGG GTT AGA CTC AAC GTC ACC AGC AAG CTT CAA TAA GTC GAA GTT AAG CAA TTG CTT GTA CAA TTC ATC CAT GCC ATG TGT AAT CC (SEQ ID NO: 16) |
| C339 | eGFP_P2A_rev | TGG ACC TGG GTT TTC CTC AAC GTC ACC AGC TTG CTT AAG CAA AGA GAA GTT AGT AGC CTT GTA CAA TTC ATC CAT GCC ATG TGT AAT CC (SEQ ID NO: 17) |
| C340 | eGFP_T2A_rev | TGG ACC TGG GTT TTC CTC AAC GTC ACC GCA AGT AAG CAA AGA ACC TCT ACC CTC AGC TCT CTT GTA CAA TTC ATC CAT GCC ATG TGT AAT CC (SEQ ID NO: 18) |
| C341 | sTomato_FMDV2A_fwd_ mit Startcodon | CAA TTG CTT AAC TTC GAC TTA TTG AAG CTT GCT GGT GAC GTT GAG TCT AAC CCA GGT CCA ATG GTT TCT AAG GGT GAG GAA GTT ATC AAG GAG (SEQ ID NO: 19) |
| C342 | sTomato_FMDV2A_fwd_ ohne Startcodon | CAA TTG CTT AAC TTC GAC TTA TTG AAG CTT GCT GGT GAC GTT GAG TCT AAC CCA GGT CCA GTT TCT AAG GGT GAG GAA GTT ATC AAG GAG TTC ATG (SEQ ID NO: 20) |
| C343 | sTomato_P2A_fwd | GCT ACT AAC TTC TCT TTG CTT AAG CAA GCT GGT GAC GTT GAG GAA AAC CCA GGT CCA GTT TCT AAG GGT GAG GAA GTT ATC AAG GAG TTC ATG (SEQ ID NO: 21) |
| C344 | sTomato_T2A_fwd | AGA GCT GAG GGT AGA GGT TCT TTG CTT ACT TGC GGT GAC GTT GAG GAA AAC CCA GGT CCA GTT TCT AAG GGT GAG GAA GTT ATC AAG GAG TTC ATG (SEQ ID NO: 22) |
| C345 | sTomato_NotI_rev | TAT GCG GCC GCT TAC TTA TAA AGC TCG TCC ATA CCG TAC AAG AAC AAG (SEQ ID NO: 23) |
| C346 | sTomato_EcoRI_fwd | AAA TGA ATT CCG AAA CGA TGG TTT CTA AGG GTG AGG AAG TTA TCA AGG AG (SEQ ID NO: 24) |
| C347 | sTomato_FMDV2A_rev | TGG ACC TGG GTT AGA CTC AAC GTC ACC AGC AAG CTT CAA TAA GTC GAA GTT AAG CAA TTG CTT ATA AAG CTC GTC CAT ACC GTA CAA GAA CAA G (SEQ ID NO: 25) |
| C348 | sTomato_P2A_rev | TGG ACC TGG GTT TTC CTC AAC GTC ACC AGC TTG CTT AAG CAA AGA GAA GTT AGT AGC CTT ATA AAG CTC GTC CAT ACC GTA CAA GAA CAA G (SEQ ID NO: 26) |

TABLE 3-continued

Primers used for the assembly of polycistronic expression constructs coding for eGFP and sTomato.

| # | Name | Sequence (5'→3') |
|---|---|---|
| C349 | sTomato_T2A_rev | TGG ACC TGG GTT TTC CTC AAC GTC ACC GCA AGT AAG CAA AGA ACC TCT ACC CTC AGC TCT CTT ATA AAG CTC GTC CAT ACC GTA CAA GAA CAA G (SEQ ID NO: 27) |
| C350 | eGFP_FMDV2A_fwd | CAA TTG CTT AAC TTC GAC TTA TTG AAG CTT GCT GGT GAC GTT GAG TCT AAC CCA GGT CCA GCT AGC AAA GGA GAA GAA CTT TTC ACT GGA G (SEQ ID NO: 28) |
| C351 | eGFP_P2A_fwd | GCT ACT AAC TTC TCT TTG CTT AAG CAA GCT GGT GAC GTT GAG GAA AAC CCA GGT CCA GCT AGC AAA GGA GAA GAA CTT TTC ACT GGA G (SEQ ID NO: 29) |
| C352 | eGFP_T2A_fwd | AGA GCT GAG GGT AGA GGT TCT TTG CTT ACT TGC GGT GAC GTT GAG GAA AAC CCA GGT CCA GCT AGC AAA GGA GAA GAA CTT TTC ACT GGA G (SEQ ID NO: 30) |
| C353 | eGFP_NotI_rev | TAT TGC GGC CGC TTA CTT GTA CAA TTC ATC CAT GCC ATG TGT AAT CC (SEQ ID NO: 31) |
| C385 | sTomato_Gibson_rev | CTC TCA GGC AAA TGG CAT TCT GAC ATC CTC TTG AGC GGC CGC TTA CTT ATA AAG CTC GTC CAT ACC GTA CAA GAA CAA G (SEQ ID NO: 32) |
| C386 | eGFP_Gibson_rev | CTC TCA GGC AAA TGG CAT TCT GAC ATC CTC TTG AGC GGC CGC TTA CTT GTA CAA TTC ATC CAT GCC ATG TGT AAT CC (SEQ ID NO: 33) |
| C389 | eGFP_AOX_Gibson_His_fwd | ACG ACA ACT TGA GAA GAT CAA AAA ACA ACT AAT TAT TGA AAG AAT TCC GAA ACG ATG CAC CAC CAT CAC CAC CAT GCT AGC AAA GGA GAA GAA CTT TTC ACT G (SEQ ID NO: 34) |
| C390 | sTomato_AOX_Gibson_His_fwd | ACG ACA ACT TGA GAA GAT CAA AAA ACA ACT AAT TAT TGA AAG AAT TCC GAA ACG ATG CAC CAC CAT CAC CAC CAT GTT TCT AAG GGT GAG GAA GTT ATC AAG GAG (SEQ ID NO: 35) |
| C391 | eGFP_GAP_Gibson_His_fwd | GTC CCT ATT TCA ATC AAT TGA ACA ACT ATC AAA ACA CAG AAT TCC GAA ACG ATG CAC CAC CAT CAC CAC CAT GCT AGC AAA GGA GAA GAA CTT TTC ACT G (SEQ ID NO: 36) |
| C392 | sTomato_GAP_Gibson_His_fwd | GTC CCT ATT TCA ATC AAT TGA ACA ACT ATC AAA ACA CAG AAT TCC GAA ACG ATG CAC CAC CAT CAC CAC CAT GTT TCT AAG GGT GAG GAA GTT ATC AAG GAG (SEQ ID NO: 37) |

TABLE 4

Primers used for the assembly of the polycistronic expression construct coding for the β-carotene biosynthesis pathway

| # | Name | Sequence (5'→3') |
|---|---|---|
| C455 | pAOX1_crtE_fw | CGA CAA CTT GAG AAG ATC AAA AAA CAA CTA ATT ATT GAA AGA ATT CCG AAA CGA TGA CGG TCT GC (SEQ ID NO: 38) |
| C456 | crtE_T2A_rev | TGG ACC TGG GTT TTC CTC AAC GTC ACC GCA AGT AAG CAA AGA ACC TCT ACC CTC AGC TCT ACT GAC GGC AGC GAG TTT TTT GTC (SEQ ID NO: 39) |
| C457 | crtB_T2A_fw | AGA GCT GAG GGT AGA GGT TCT TTG CTT ACT TGC GGT GAC GTT GAG GAA AAC CCA GGT CCA AAT AAT CCG TCG TTA CTC AAT CAT GCG G (SEQ ID NO: 40) |
| C458 | crtB_T2A_rev | AGG TCC AGG ATT CTC TTC GAC ATC TCC GCA GGT CAA AAG GGA TCC ACG TCC TTC GGC ACGGAG CGG GCG CTG CCA GAG ATG (SEQ ID NO: 41) |
| C459 | crtI_T2A_fw | CGT GCC GAA GGA CGT GGA TCC CTT TTG ACC TGC GGA GAT GTC GAA GAG AAT CCT GGA CCT AAA CCA ACT ACG GTA ATT GGT GCA GG (SEQ ID NO: 42) |
| C460 | crtI_T2A_rev | TGG TCC GGG ATT TTC TCC ACG TCG CCA CAA GTC AGC AAT GAG CCA CGA CCT TCT GCT CTA TCA GAT CCT CCA GCA TCA AAC CTG C (SEQ ID NO: 43) |

TABLE 4-continued

Primers used for the assembly of the polycistronic expression construct coding for the β-carotene biosynthesis pathway

| # | Name | Sequence (5'→3') |
|---|---|---|
| C461 | crtY_T2A_fw | AGA GCA GAA GGT CGT GGC TCA TTG CTG ACT TGT GGC GAC GTG GAG GAA AAT CCC GGA CCA CAA CCG CAT TAT GAT CTG ATT CTC GTG G (SEQ ID NO: 44) |
| C462 | crtY_AOX_TT_rev | CAG GCA AAT GGC ATT CTG ACA TCC TCT TGA GCG GCC GCT TAA CGA TGA GTC G (SEQ ID NO: 45) |
| C463 | pGAP_crtE_fw | GTC CCT ATT TCA ATC AAT TGA ACA ACT ATC AAA ACA CAG AAT TCC GAA ACG ATG ACG GTC TGC (SEQ ID NO: 46) |
| C464 | crtB_FMDV2A_rev | TGG ACC TGG GTT AGA CTC AAC GTC ACC AGC AAG CTT CAA TAA GTC GAA GTT AAG CAA TTG GAG CGG GCG CTG CCA GAG ATG (SEQ ID NO: 47) |
| C465 | crtI_FMDV2A_fw | CAA TTG CTT AAC TTC GAC TTA TTG AAG CTT GCT GGT GAC GTT GAG TCT AAC CCA GGT CCA AAA CCA ACT ACG GTA ATT GGT GCA GG (SEQ ID NO: 48) |
| C466 | crtI_P2A_rev | TGG ACC TGG GTT TTC CTC AAC GTC ACC AGC TTG CTT AAG CAA AGA GAA GTT AGT AGC TAT CAG ATC CTC CAG CAT CAA ACC TGC (SEQ ID NO: 49) |
| C468 | crtY_P2A_fw | GCT ACT AAC TTC TCT TTG CTT AAG CAA GCT GGT GAC GTT GAG GAA AAC CCA GGT CCA CAA CCG CAT TAT GAT CTG ATT CTC GTG G (SEQ ID NO: 50) |

TABLE 5

Primers used for the assembly of the polycistronic expression construct coding for the violacein biosynthesis pathway

| # | Name | Sequence (5'→3') |
|---|---|---|
| C476 | pGAP_vioC_fw | GTC CCT ATT TCA ATC AAT TGA ACA ACT ATC AAA ACA CAG AAT TCC GAA ACG ATG AAG AGA GCT ATC ATT G (SEQ ID NO: 51) |
| C477 | pAOX1_vioC_fw | CGA CAA CTT GAG AAG ATC AAA AAA CAA CTA ATT ATT GAA AGA ATT CCG AAA CGA TGA AGA GAG CTA TCA TTG (SEQ ID NO: 52) |
| C493 | vioC_T2A4_rev | GGG TCC TGG ATT TTC TTC CAC ATC ACC GCA GGT AAG TAA GGA ACC ACG GCC CTC TGC ACG GTT AAC TCT ACC AAT CTT GTA CCA GAC GTT C (SEQ ID NO: 53) |
| C494 | T2A4_vioB_fw | CGT GCA GAG GGC CGT GGT TCC TTA CTT ACC TGC GGT GAT GTG GAA GAA AAT CCA GGA CCC TCT ATT TTG GAC TTC CCA AGA ATC CAC TTT C (SEQ ID NO: 54) |
| C478 | vioB_T2A5_rev | TGG ACC AGG GTT CTC CTC GAC GTC TCC ACA TGT AAG AAG TGA TCC CCT ACC CTC GGC ACG AGC TTC ACG AGA TAA CTT CCA CAG AGC (SEQ ID NO: 55) |
| C479 | T2A5_vioE_fw | CGT GCC GAG GGT AGG GGA TCA CTT CTT ACA TGT GGA GAC GTC GAG GAG AAC CCT GGT CCA GAA AAC CGT GAG CCA CCT TTG C (SEQ ID NO: 56) |
| C480 | vioE_T2A6_rev | AGG ACC GGG GTT CTC TTC AAC ATC GCC ACA CGT TAA CAG GGA ACC CCT TCC TTC AGC TCT TCT CTT AGC GGC GAA GAC AGC G (SEQ ID NO: 57) |
| C481 | T2A6_vioD_fw | AGA GCT GAA GGA AGG GGT TCC CTG TTA ACG TGT GGC GAT GTT GAA GAG AAC CCG GTC CTA AGA TCT TGT GAT TGG TGC AGG AC (SEQ ID NO: 58) |
| C482 | vioD_T2A7_rev | TGG GCC GGG ATT CTC CTC TAC ATC ACC ACA AGT CAA CAG GGA TCC TCT GCC TTC TGC CCT TCT TTG CAA GGC GTA TCT AAG GTT TTG TG (SEQ ID NO: 59) |
| C483 | T2A7_viokfw | AGG GCA GAA GGC AGA GGA TCC CTG TTG ACT TGT GGT GAT GTA GAG GAG AAT CCC GGC CCA AAA CAC TCT TCC GAC ATT TGT ATT GTC G (SEQ ID NO: 60) |

TABLE 5-continued

Primers used for the assembly of the polycistronic expression construct coding for the violacein biosynthesis pathway

| # | Name | Sequence (5'→3') |
|---|---|---|
| C484 | vioA_AOX_TT_rev | CAG GCA AAT GGC ATT CTG ACA TCC TCT TGA GCG GCC GCT TAG GCA GCA ATT CTT TGC AAA AGC AAA C (SEQ ID NO: 61) |

TABLE 6

Primers used for the assembly of the polycistronic expression construct coding for the β-carotene and the violacein biosynthesis pathway

| # | Name | Sequence (5'→3') |
|---|---|---|
| C485 | crtY_12A8_rev | AGG GCC TGG GTT CTC TTC CAC ATC TCC ACA AGT TAA AAG AGA GCC TCT CCC CTC CGC CCT ACG ATG AGT CGT CAT AAT GGC TTG C (SEQ ID NO: 62) |
| C486 | T2A8_vioC_fw | AGG GCG GAG GGG AGA GGC TCT CTT TTA ACT TGT GGA GAT GTG GAA GAG AAC CCA GGC CCT AAG AGA GCT ATC ATT GTT GGT GGA GG (SEQ ID NO: 63) |
| C487 | T2A_crtE_fw | AGA GCT GAG GGT AGA GGT CTT TGC TTA CTG CGG TGA CGT TGA GGA AAC CCA GGT CCA GAA TTC GAA ACG ATG ACG GTC TGC (SEQ ID NO: 64) |
| C488 | crtB_T2A_rev | TGG ACC TGG GTT TTC CTC AAC GTC ACC GCA AGT AAG CAA AGA ACC TCT ACC CTC AGC TCT GAG CGG GCG CTG CCA GAG ATG (SEQ ID NO: 65) |
| C489 | 12A_crtI_fw | AGA GCT GAG GGT AGA GGT CTT TGC TTA CTG CGG TGA CGT TGA GGA AAC CCA GGT CCA AAA CCA ACT ACG GTA ATT GGT GCA GG (SEQ ID NO: 66) |
| C490 | crtI_T2A_rev | TGG ACC TGG GTT TTC CTC AAC GTC ACC GCA AGT AAG CAA AGA ACC TCT ACC CTC AGC TCT TAT CAG ATC CTC CAG CAT CAA ACC TGC (SEQ ID NO: 67) |
| C491 | T2A_crtY_fw | AGA GCT GAG GGT AGA GGT CTT TGC TTA CTG CGG TGA CGT TGA GGA AAC CCA GGT CCA CAA CCG CAT TAT GAT CTG ATT CTC GTG G (SEQ ID NO: 68) |
| C492 | crtY_T2A_rev | TGG ACC TGG GTT TTC CTC AAC GTC ACC GCA AGT AAG CAA AGA ACC TCT ACC CTC AGC TCT GCG CCG CTA ACG ATG AGT CG (SEQ ID NO: 69) |
| C514 | pGAP_viok_fw | GTC CCT ATT TCA ATC AAT TGA ACA ACT ATC AAA ACA CAG AAT TCC GAA ACG ATG AAA CAC TCT TCC GAC ATT GTT ATT GTC G (SEQ ID NO: 70) |
| C515 | pAOX_viok_fw | CGA CAA CTT GAG AAG ATC AAA AAA CAA CTA ATT ATT GAA AGA ATT CCG AAA CGA TGA AAC ACT CTT CCG ACA TTT GTA TTG TCG (SEQ ID NO: 71) |
| C531 | vioC_opt_T2A8_rev | AGG GCC TGG GTT CTC TTC CAC ATC TCC ACA AGT TAA AAG AGA GCC TCT CCC CTC CGC CCT GTT AAC TCT ACC AAT CTT GTA CCA GAC G (SEQ ID NO: 72) |
| C532 | T2A8_crtE_fw | AGG GCG GAG GGG AGA GGC TCT CTT TTA ACT TGT GGA GAT GTG GAA GAG AAC CCA GGC CCT ACG TCT GCA AAA AAA CAC G (SEQ ID NO: 73) |
| C462 | crtY_AOX_TT_rev | CAG GCA AAT GGC ATT CTG ACA TCC TCT TGA GCG GCC GCT TAA CGA TGA GTC G (SEQ ID NO: 74) |

TABLE 7

Primers used for the assembly of the bidirectional and polycistronic expression construct coding for the β-carotene and the violacein biosynthesis pathway

| # | Name | Sequence (5'→3') |
|---|------|------------------|
| C533 | DAS1TT_viokfw | CTC CTA ACT AAA ACT GTA AAG ACT TCC CGT ACT AGT TTA GGC AGC AAT TCT TTG CAA AAG CAA ACG (SEQ ID NO: 75) |
| C534 | HTX1_vioB_rev | GAA AGT GGA TTC TTG GGA AGT CCA AAA TAG ACA TTT TGA TTT GTT TAG GTA ACT TGA ACT GGA TGT ATT AGT TTG (SEQ ID NO: 76) |
| C549 | vioB_TBF4_Fw_new | GTG GAA AGT TAT CTC GTG AAG CTT AAG TAC GTA GTT TCG CTT AGT TTA AGA CTA AAC TAA TGT TG (SEQ ID NO: 77) |
| 550 | TBF4_vioE_rev_new | CGC TGT CTT CGC CGC TAA GAG ATA AGC CGA ATA GTT TGT ATA CGT CTT ATG TAA TGA GTT TC (SEQ ID NO: 78) |
| C536 | vioE_HHX1_fw | GCA AAG GTG GCT CAC GGT TTT CCA TTT TTC TTT ACC TGG ATA TAA ATA AAA AAA GGA AAC ACA ATC TC TG (SEQ ID NO: 79) |
| C537 | HHX1_vioD_rev | CCT GCA CCA ATC ACA AGG ATC TTC ATG TTT TAT CGA TAG TAG TTG AGC AAT AAA AAA AAG GAG AAA AAG C (SEQ ID NO: 80) |
| C545 | vioD_DAS2TT_fw | CCT TAG ATA CGC CTT GCA AAG ATA AGT AGA TTT GGC CAC TAA CGG GTT AGT AG (SEQ ID NO: 81) |
| C546 | DAS2TT_GAP_rev | GGA CAC CAA GAC ATT TCT ACA AAA AGA CGG GGT TCG TAA ACT GGT TCC (SEQ ID NO: 82) |
| C547 | DAS2TT_GAP_fw | GAG GAA CCA GTT TAC GAA CCC CGT CTT TTT GTA GAA ATG TCT TGG TGT CCT CGT CC (SEQ ID NO: 83) |
| C538 | GAP_vioC_rev | CAC CAA CAA TGA TAG CTC TCT TCA TTG TGT TTT GAT AGT TGT TCA ATT GAT TGA AAT AGG GAC (SEQ ID NO: 84) |
| C539 | BZ6_vioB_rev | GAT TCT TGG GAA GTC CAA AAT AGA CAT TTT TGA TGT TTG ATA GTT TGA TAA GAG TGA ACT TTA GTG TTT AG (SEQ ID NO: 85) |
| C540 | vioE_BZF8_fw | GCA AAG GTG GCT CAC GGT TTT CCA TCT TAG ATT TTT TTT TTT GCT TGG TGG GAT TCC TTC G (SEQ ID NO: 86) |
| C541 | BZF8_vioD_rev | CTG CAC CAA TCA CAA GGA TCT TCA TTG TGA ATA TCA AGA ATT GTA TGA ACA AGC AAA GTT GG (SEQ ID NO: 87) |
| C542 | DAS2TT_FDH1_fw | GGA ACC AGT TTA CGA ACC CGT CTG GGT GCA GGA ACC AGC TTC TAA TTA AAT AG (SEQ ID NO: 88) |
| C543 | FDH1_vioC_rev | CAC CAA CAA TGA TAG CTC TCT TCA TTG TTT AAG TGG GTG ATG TTG GAG GTA TTT G (SEQ ID NO: 89) |
| C549 | vioB_TBF4_Fw_new | GTG GAA AGT TAT CTC GTG AAG CTT AAG TAC GTA GTT TCG CTT AGT TTA AGA CTA AAC TAA TGT TG (SEQ ID NO: 90) |
| C550 | TBF4_vioE_rev_new | CGC TGT CTT CGC CGC TAA GAG ATA AGC CGA ATA GTT TGT ATA CGT CTT ATG TAA TGA GTT TC (SEQ ID NO: 91) |

TABLE 8

Primers used for the assembly of the polycistronic expression construct harboring ubiquitin as additional linker.

| Name | Sequence (5'→3') |
|------|------------------|
| T2A_Ubiqitin_GFP_fw | AGA GCT GAG GGT AGA GGT TCT TTG CTT AC (SEQ ID NO: 92) |
| T2A_Ubiqitin_GFP_rev | GGG ACA ACT CCA GTG AAA AGT TCT TCT CC (SEQ ID NO: 93) |
| Ubiquitin_GFP_fw | GCA CTT GGT CCT TAG ACT TAG AGG AGG TA TGG CTA GCA AAG GAG AAG AAC TTT TCA CTG (SEQ ID NO: 94) |
| Ubiquitin_GFPohne_fw | GCA CTT GGT CCT TAG ACT TAG AGG AGG TG CTA GCA AAG GAG AAG AAC TTT TCA CTG (SEQ ID NO: 95) |
| Ubiquitin_GFPohne_rev | CAG TGA AAA GTT CTT CTC CTT TGC TAG CAC CTC CTC TAA GTC TAA GGA CCA AGT GC (SEQ ID NO: 96) |

TABLE 8-continued

Primers used for the assembly of the polycistronic expression construct harboring ubiquitin as additional linker.

| Name | Sequence (5'→3') |
|---|---|
| eGFP_Gibson_rev | CTC TCA GGC AAA TGG CAT TCT GAC ATC CTC TTG AGC GGC CGC TTA CTT GTA CAA TTC ATC CAT GCC ATG TGT AAT CC (SEQ ID NO: 97) |
| sTomato_AOX_Gibson_His_fwd | ACG ACA ACT TGA GAA GAT CAA AAA ACA ACT AAT TAT TGA AAG AAT TCC GAA ACG ATG CAC CAC CAT CAC CAC CAT GTT TCT AAG GGT GAG GAA GTT ATC AAG GAG (SEQ ID NO: 98) |
| sTomato_T2A_rev | TGG ACC TGG GTT TTC CTC AAC GTC ACC GCA AGT AAG CAA AGA ACC TCT ACC CTC AGC TCT CTT ATA AAG CTC GTC CAT ACC GTA CAA GAA CAA G (SEQ ID NO: 99) |

Cultivation of *P. pastoris* Strains

Protein expression in *P. pastoris* was performed essentially as described in [13]. Therefore, *Pichia* cultures were grown in buffered minimal dextrose (BMD) or buffered mineral methanol (BMM) medium containing 200 mM $KP_i$, pH 6.0, 13.4 g/L yeast nitrogen base and 0.4 mg/L biotin supplemented with 2% (w/v) glucose or 5% (v/v) methanol, respectively.

Fluorescence Measurements

For the measurement of fluorescence 190 µL dd$H_2O$ were mixed with 10 µL of liquid cultures of *P. pastoris* strains. Fluorescence of eGFP (488 nm excitation, 507 nm emission) and sTomato (544 nm excitation, 581 nm emission) was recorded with a Synergy MX Microplate Reader.

SDS-PAGE/Immunoblot Analysis

Protein isolation from yeast was performed with the Y-PER™ Yeast Protein Extraction Reagent from Thermo Scientific Inc. according to the manufacturer's instructions. The total protein concentrations of the obtained samples were determined by the Bio-Rad protein assay (Bio-Rad Laboratories GmbH, Germany) using BSA as standard. 2 µg of total protein per lane were separated by SDS-PAGE under reducing conditions using NuPAGE® 4-12% Bis-Tris gel (Invitrogen). Protein bands were transferred onto a nitrocellulose membrane (GE Healthcare, Chalfont St Giles, UK) electrophoretically in a wet blotting system. Immunoblot detection was performed using a HIS-specific antibody (Tetra His-antibody from Quiagen) as primary antibody as well as Goat Anti-Mouse IgG (H+L)-HRP from Invitrogen as secondary antibody according to the manual provided by the supplier.

Product Analysis

A small pellet of coloured *Pichia* cells was resuspended in 1 mL yeast lysis buffer (1 M sorbitol, 100 mM EDTA, 14 mM β-mercaptoethanol). 100 µL of a zymolyase stock solution (1000 U/mL) were added and the reaction mixture was incubated at 30° C. for 30 min. The thus generated spheroplasts were pelleted by centrifugation (5 min, max. speed) and resuspended in 500 µL MeOH. Pigments were extracted by incubating the mixture twice for 15 min at 60° C. The combined organic phases were dried using a stream of dry nitrogen gas and dissolved in 100 µL MeOH. Extracts were subjected to TLC using an ethyl acetate/cyclohexane solvent system (9:1).

Example 1—Identification of Functional 2A Sequences

The performance of different 2A sequences in that yeast was evaluated (see Table 8). Functional ones were employed to express various biosynthesis pathways. Surprisingly, up to nine genes were expressed as active enzymes delivering strains producing the desired pathway metabolites.

TABLE 9

2A sequences investigated for polycistronic expression in *P. pastoris*.

| 2A sequence | Origin | Amino acid sequence | Reference |
|---|---|---|---|
| FMDV2A | Foot-and-mouth-disease virus | QLLNFDLLKLAGDVESNPGP (SEQ ID NO: 11) | [2] |
| T2A | *Thosea asigna* virus | RAEGRGSLLTCGDVEENPGP (SEQ ID NO: 12) | [12] |
| P2A | *Porcine teschovirus*-1 | ATNFSLLKQAGDVEENPGP (SEQ ID NO: 13) | [12] |
| F2A* | Defective FMDV 2A sequence | QLLNFDLLKLAGDVESNPGA (SEQ ID NO: 14) | [3] |

In a first step, a set of different 2A sequences was tested for functionality in *P. pastoris* the P2A sequence of porcine teschovirus-1, the T2A sequence of Thosea asigna virus and the FMDV2A sequence of the foot-and-mouth disease virus. The defective 2A sequence F2A served as negative control [3]. Therefore, a fusion construct of the two fluorescent proteins eGFP and sTomato was generated as schematically depicted in FIG. 1. The genes of eGFP and sTomato were fused only via the 2A sequences shown in Table 8 without any further linker. Thereby, the stop codon of the first gene in the polycistronic construct was omitted as well as the start codon of the subsequent gene. To evaluate if differences can be observed when the start codon is present on the second coding sequence, an additional construct pPp_T4_S_eGFP_FMDV2A_sTomato_withATG was generated. The gene fusion was placed either behind the AOX1 or GAP promoter. In addition, a 6×His-Tag was added to the N-terminus of the gene fusion to allow Western blot analysis of the resulting gene products. To examine whether the position of the genes in the polycistronic construct does affect the respective expression levels, two series of constructs were generated harbouring either the fusion eGFP_sTomato or sTomato_eGFP.

The expression constructs were used to transform *P. pastoris* and the resulting transformants were screened for eGFP and sTomato fluorescence, respectively. In FIG. 2 the screening results are exemplarily shown for the constructs pPp_T4_S_eGFP_P2A_sTomato (panel A and C) and pPp_T4_S_sTomato_P2A_eGFP. All tested transformants showed green (eGFP) and red (sTomato) fluorescence indicating that both proteins were functionally expressed. In addition, the corresponding fluorescence levels did not change significantly depending on the gene position in the polycistronic construct. However, the position on the single transcript might affect the expression levels in case that other more complex proteins are produced and/or more than two proteins are produced coordinately.

Figure 3:
FIG. 3: Western blot analysis of crude cell lysates of *P. pastoris* strains expressing different 2A constructs under the control of $P_{AOX1}$ (upper panel) or $P_{GAP}$ (lower panel) using anti-His antibody. The expected bands of the uncleaved protein fusion (55 kDa) and the single fluorescence proteins (27 kDa) are indicated. Lane 1: eGFP-T2A-sTomato; 1*: eGFP-T2A-sTomato, multicopy strain; 2: sTomato-T2A-eGFP; 3: eGFP-FMDV2A (with start codon)-sTomato; 4: eGFP-FMDV2A (without start codon)-sTomato; 5: sTomato-FMDV2A-eGFP; 6: eGFP-P2A-sTomato; 7: sTomato-P2A-eGFP; 8: eGFP-F2A-sTomato; 9: sTomato-F2A-eGFP; 10: *P. pastoris* CBS 7435.
Figure 3:

Western blot analysis employing anti-bodies binding to the N-terminally attached His-tag was conducted to investigate whether the fluorescent proteins are present as fusions (~55 kDa) or as separate proteins (~27 kDa). In the case of $P_{AOX1}$ driven expression, bands indicating the presence of separate fluorescence proteins as well as of the protein fusion were detected for all tested 2A sequences (FIG. 3, upper panel). Also in the negative control eGFP-F2A-sTomato a band for His-tagged eGFP was observed. In this construct, the two fluorescent proteins were separated by a defective 2A sequence which contains a PGA instead of the PGP required for the ribosomal skip. The second negative control (sTomato-F2A-eGFP) only showed the expected band corresponding to the fusion product. Therefore the sequences surrounding the 2A sequences might have an influence on the ribosomal skipping mechanism too or represent a target for endogenous proteases causing protein cleavage.

In the case of $P_{GAP}$ driven gene expression, only the constructs based on the T2A and P2A sequences resulted in separate fluorescence proteins (FIG. 3, lower panel). Employing the FMDV2A as well as the defective F2A sequence only yielded the fusion product. It still needs to be clarified why the obtained results for $P_{AOX1}$ and $P_{GAP}$ are not the same. However, it was clearly shown that the 2A sequences from Thosea asignus virus and porcine teschovirus-1 are functional in *P. pastoris* allowing the coordinate expression of two genes and significant amounts of separate proteins.

Figure 4:
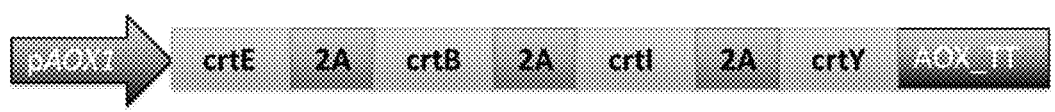
FIG. 4: Schematic representation of the polycistronic expression construct coding for the β-carotene biosynthesis pathway. All four pathway genes were fused to a single transcript separated only by T2A sequences.
Figure 5:
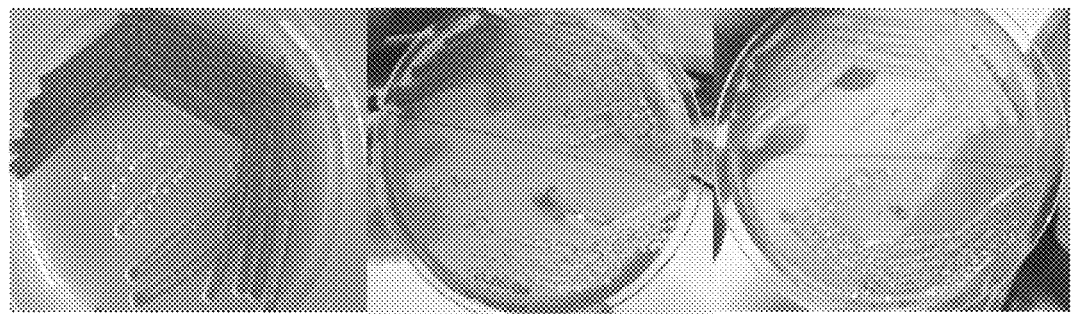
FIG. 5: *P. pastoris* strains harboring the four carotenoid pathway genes under the separate control of $P_{GAP}$. Functional pathway expression is indicated by the formation of orange colored cells due to β-carotene accumulation. The majority of the investigated recombinant strains displayed a heterogeneous phenotype indicating strain stability issues.

Example 2—Polycistronic Expression of the β-carotene and the Violacein Biosynthesis Pathway To determine whether the 2A sequences can also be exploited for the recombinant expression of multi-gene pathways the β-carotene biosynthesis pathway from *P. ananatis* was assembled to a polycistronic expression construct as shown in FIG. 4.

The functional expression of this pathway in *P. pastoris* was already described in literature and was based on a co-expresssion construct harboring all four pathway genes under the separate control of the GAP promoter [14]. However, reproducing this expression construct and transforming *P. pastoris* with such construct yielded a broad range of transformants with varying phenotype. Strains displaying a homogenous orange phenotype due to β-carotene accumulation were hardly observed. The majority of transformants had a heterogenous phenotype, i.e. orange cells were overgrown by white ones to a greater or lesser extend. These findings might indicate severe issues with the genetic stability of the corresponding strains. The same results can be observed when employing the inducible AOX1 promoter, but to a lesser extend.

Analysis of orange and white colonies by colony PCR revealed that the latter ones have lost either one or several pathway genes (data not shown). The repetitive homologous promoter and terminator sequences might be responsible for recombination events removing foreign DNA sequences, especially if the corresponding gene products constitute a burden to the cell (e.g. toxic compounds formed).

Figure 6:
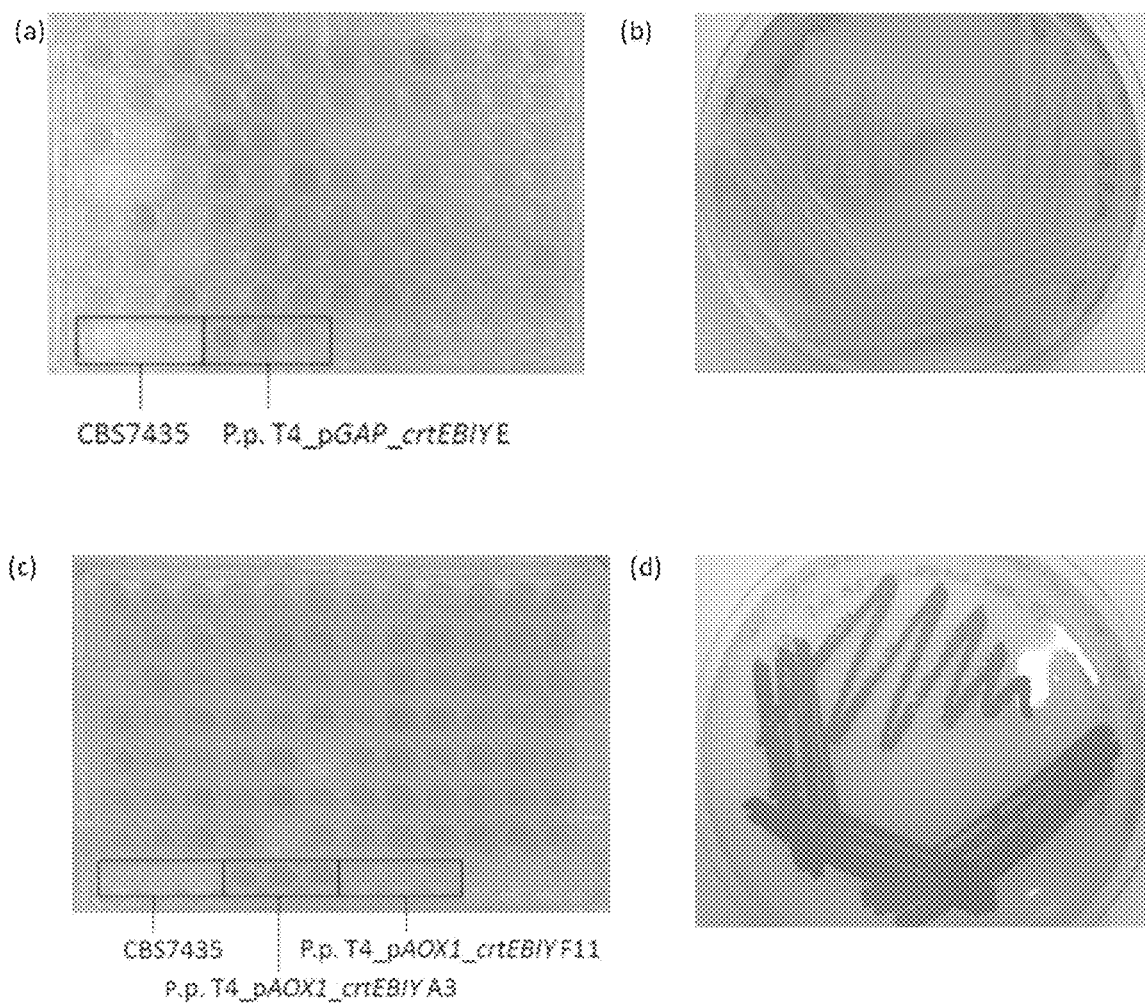
FIG. 6: *P. pastoris* strains expressing the β-carotene biosynthesis pathway from a single polycistronic construct based on T2A sequences under the control of the $P_{GAP}$ (a and b) or under the control of $P_{AOX1}$ (c+d).

The first polycistronic expression of the carotenoid pathway in *P. pastoris* based on 2A sequences was successful: the majority of 84 randomly picked transformants showed the formation of the orange pigment (FIG. 6). Based on the colour development one can deduce that the obtained expression levels are comparable to those obtained with strains based on co-expression constructs with separate regulatory elements per pathway gene. In addition, the 2A sequences based strains displayed a stable phenotype: non of the investiged strains showed the appearance of white colonies. These findings indicate that the strain stability is improved by employing 2A sequences instead of repetitive regulatory elements as described previously also for the shorter 3 gene carotenoid pathway in baker's yeast [5]. The (long-term) stability of the corresponding strains is currently under investigation.

Figure 7:
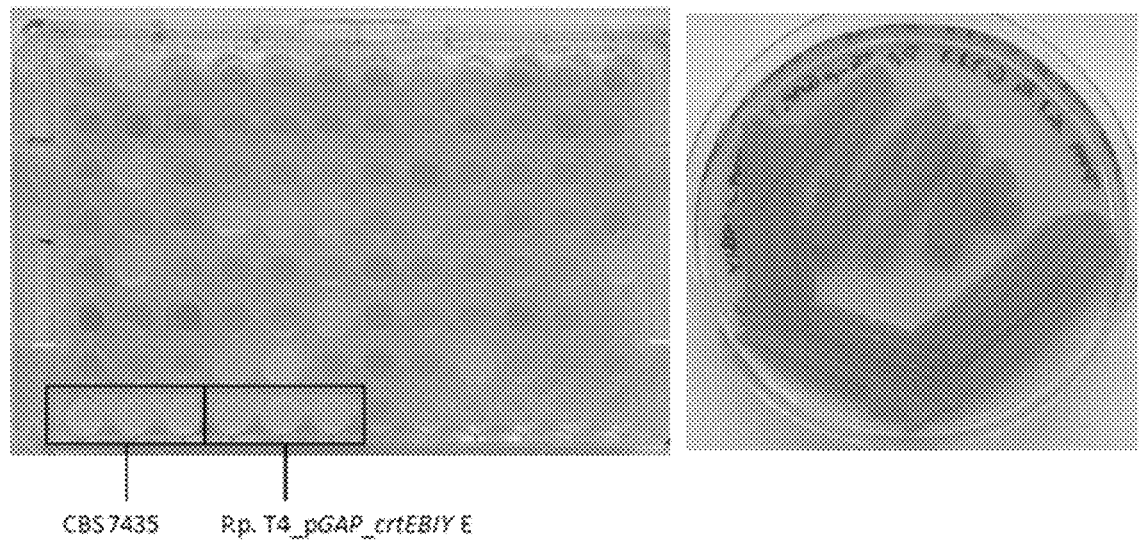
FIG. 7: *P. pastoris* strains constitutively expressing the β-carotene biosynthesis pathway from a single polycistronic construct based on T2A and P2A sequences.

In addition, the β-carotene pathway was assembled by employing alternately the 2A sequences from Thosea asignus virus and porcine teschovirus-1. Also this strategy resulted in functional and stable *P. pastoris* strains (FIG. 7) and might be considered as an option allowing fine-tuned pathway gene expression and to avoid the repeated use of homologous sequences in the assembly of long pathways with multiple genes of interest.

As a second example, we assembled a polycistronic expression construct for the violacein pathway from *C. violaceum*. This pathway consists of even five genes and yields in violacein, a natural purple pigment that exhibits antibacterial, antiviral and anti-tumorigenic properties. This pathway has not been recombinantly expressed in *P. pastoris* yet and also exceeds the number of coexpressed genes in any organisms using the 2A fusion technology so far.

Figure 8:
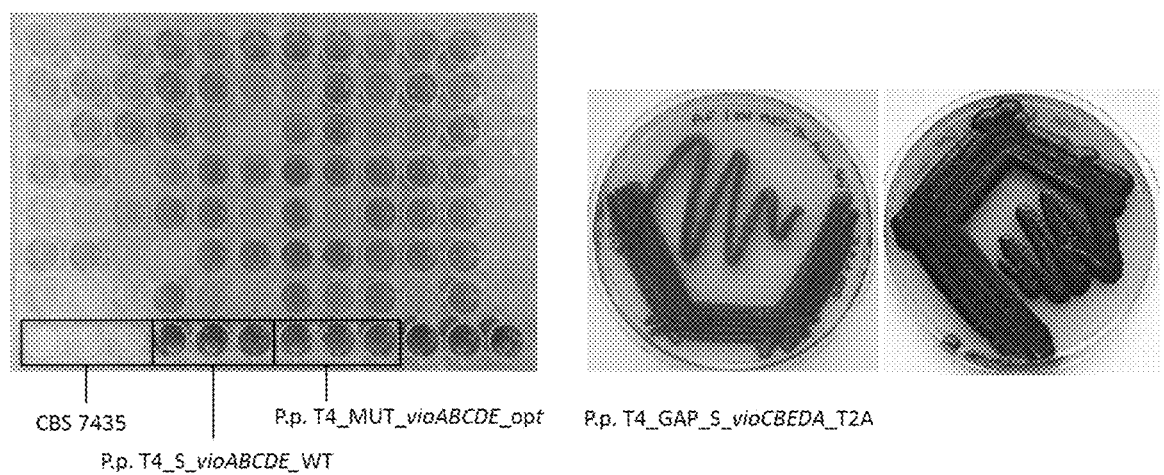
FIG. 8: *P. pastoris* strains constitutively expressing violacein pathway based on a polycistronic expression construct. The strains display a purple phenotype indicating functional pathway expression.

As shown in FIG. 8 violacein pathway expression based on T2A sequences resulted in purple colored *P. pastoris* transformants indicating functional pathway expression due to accumulation of the purple pigment. As observed for the carotenoid pathway, the resulting strains showed a homogenous colored phenotype indicating that the pathway is stable integrated.

These results clearly indicate that 2A sequences can be functionally employed to not only functionally express, but also to stably implement multi-gene pathways in *P. pastoris*.

Example 3—Polycistronic Expression of Pathways with More than Five Genes

Figure 9A:
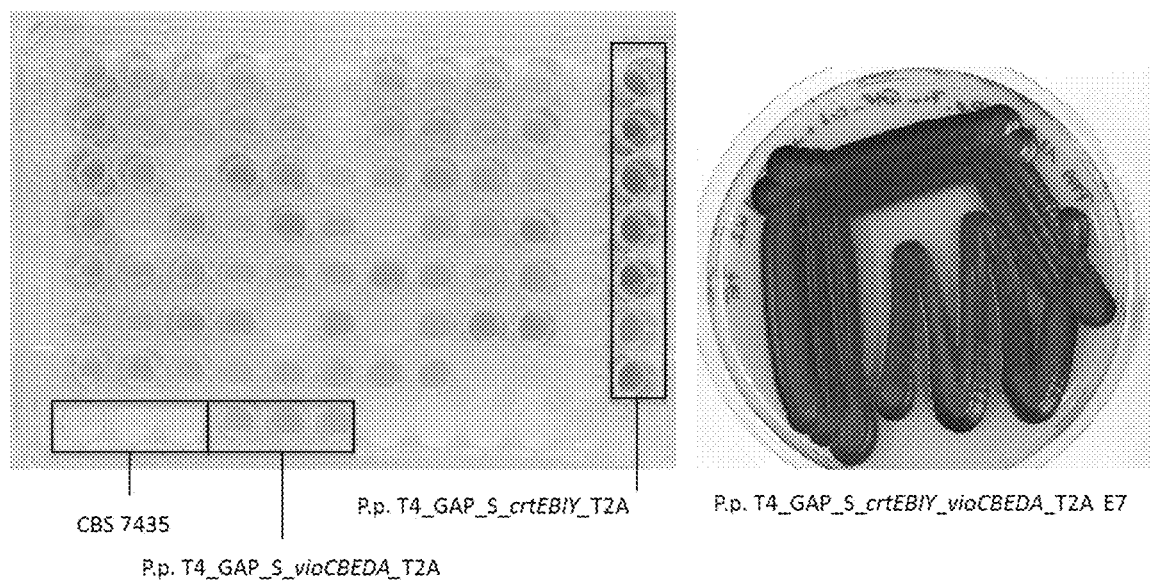
FIG. 9A: *P. pastoris* strains expressing the violacein and the carotenoid biosynthesis pathway from a single polycistronic transcript. The functional expression of both pathways is indicated by a brownish colored yeast cells.

Inspired by the fact that more genes than previously known can be coexpressed by a single set of promoter and terminator, we investigated how many genes can be functionally expressed from a polycistronic expression construct. Therefore, the genes of the carotenoid biosynthesis pathway were combined with the ones of the violacein pathway, the genes beeing individually separated by T2A sequences. The functional expression of both well known biosynthetic pathways is indicated by a brownish appearance of the yeast cells due to the accumulation of the purple and orange pigments. As shown in FIG. 9A the resulting *P. pastoris* transformants exhibited indeed a brown phenotype.

Figure 10:
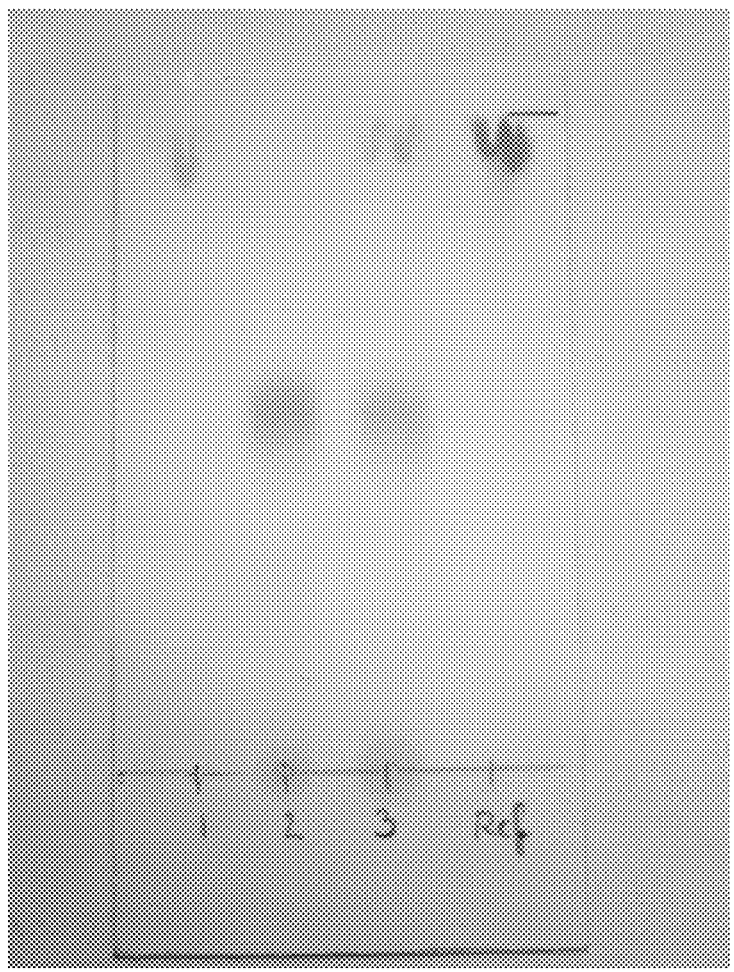
FIG. 10: Thin layer chromatography of cell extracts obtained from strains expressing the β-carotene (1), the violacein (2) and the β-carotene/violacein biosynthetic pathway (3) based on the 2A technology. β-carotene served as reference (Ref).

To further prove that the resulting strains are producing violacein and β-carotene, cell extracts were analyzed by TLC (FIG. 10). The cell extract from the *Pichia* strain expressing all nine genes in a polycistronic fashion contained the same compounds as strains expressing the β-carotene or the violacein pathway only.

Thus, it can be concluded that at least nine genes can be expressed employing 2A sequences. Up to now, only the production of pathways consisting of 3 proteins from such polycistronic constructs have been reported yet for yeasts and fungi [5, 15]. There were doubts if longer constructs can be functionally expressed due to the long transcripts which have to be produced and maintained by the cells efficiently and also due to decreasing translational products of the peptide sequence coded downstream of the 2A sequence compared to the upstream sequence. Such effects are multiplicative and we expected that long constructs containing multiple genes cannot be fully expressed anymore. However, our results indicated that 2A sequences are also suitable for the generation of pathways with even more than five genes and allow a very compact design of long expression cassettes for metabolic and synthetic pathways in eukaryotes.

Figure 9B:
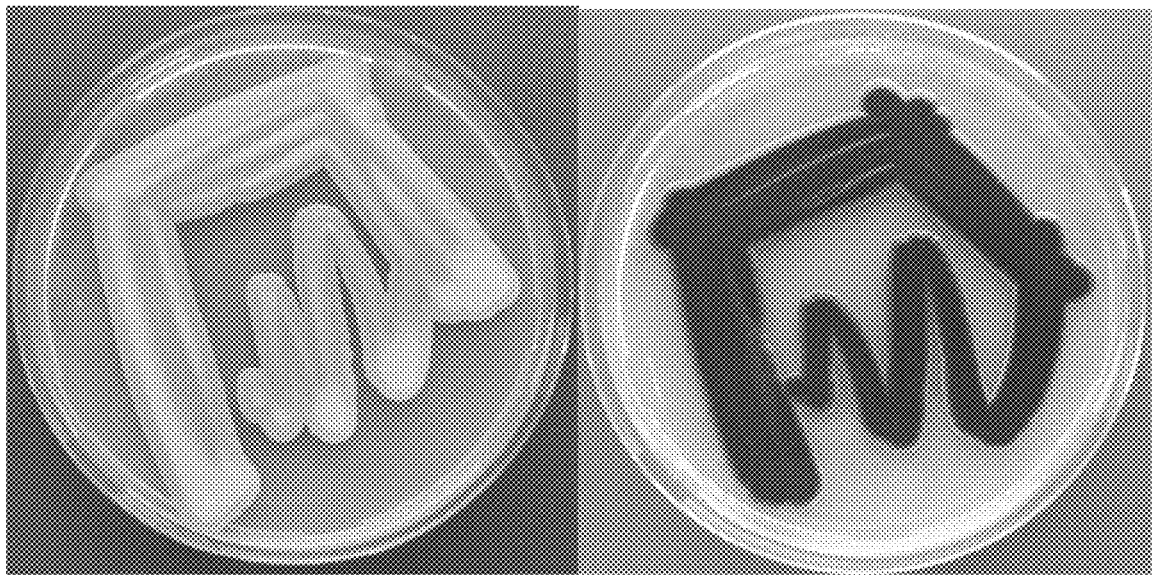
FIG. 9B: Functional expression of nine genes from a single polycistronic 2A peptide based transcript. (a) *P. pastoris* strain expressing a construct in which the carotenoid pathway genes are positioned upstream of the violacein pathway ones. (b) *P. pastoris* strain expressing a construct in which the violacein pathway genes are positioned upstream of the carotenoid pathway ones. The functional expression of both pathways is indicated by brownish coloured cells.

Example 4—Polycistronic Expression of Pathways with More than Five Genes in Different Orders Following Example 3, two constructs were generated harbouring either the carotenoid pathway genes upstream of the violacein pathway or the other way round. The size of the resulting polycistronic transcript was ~12 kb. The functional expression of both biosynthetic pathways is indicated by a brownish appearance of the yeast cells due to the accumulation of the orange and purple metabolites. As shown in FIG. 9B the resulting *P. pastoris* strains exhibited indeed a brown phenotype simultaneously producing β-carotene and violacein. However, it can be clearly seen that the order of the pathway genes in the polycistronic construct had a detrimental effect on pathway expression. If the violacein pathway genes were placed first, the resulting strains showed a clear brown phenotype already after 60 h of incubation, while the phenotype of strains harbouring the construct with the carotenoid pathway genes at the beginning was not that pronounced (but reached the same level of colour development after an extended incubation time too). Therefore, positioning individual genes on different positions within the polycistron may be considered as a way to fine tune pathway expression which is by the employment of only one promoter otherwise not possible.

Figure 11:
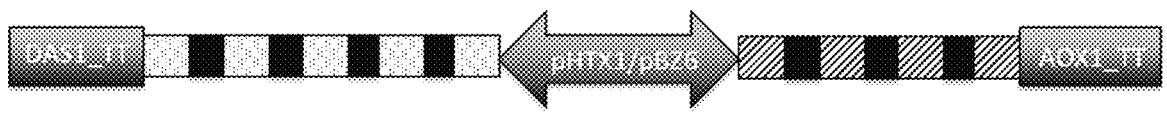
FIG. 11: Schematic representation of violacein and carotenoid pathway expression based on 2A sequences in combination with a bidirectional promoter. Constitutive ($P_{HTX1}$) as well as methanol inducible ($P_{BZ6}$) promoters were tested. Black boxes represent 2A sequences, dotted and hatched boxes represent the individual genes of the violacein and the carotenoid biosynthesis pathway, respectively.
Figure 13:
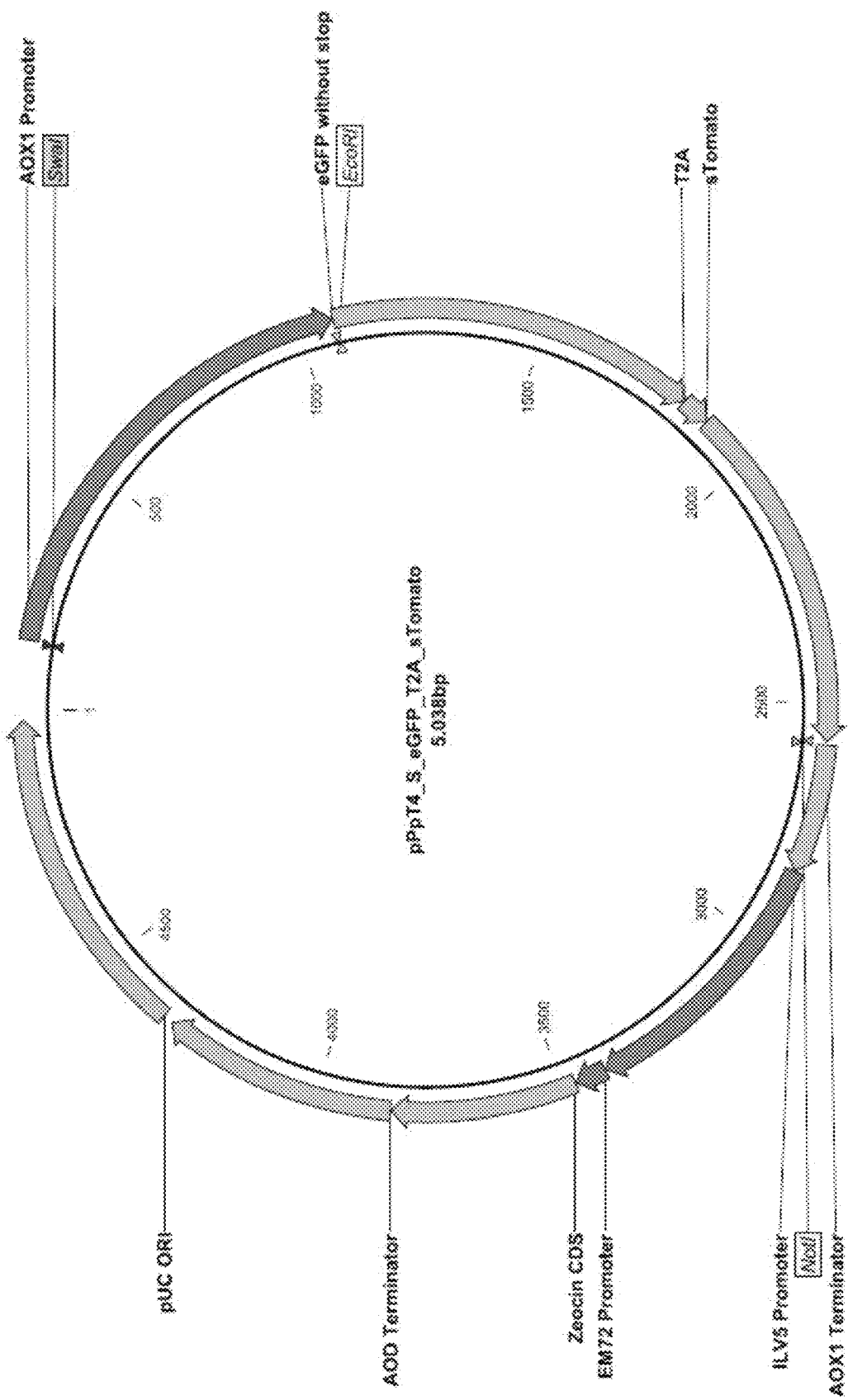
FIG. 13: Exemplary plasmid map of the expression construct pPpT4_S_eGFP_T2A_sTomato based on the inducible $P_{AOX1}$. To test polycistronic gene expression in *P. pastoris* gene fusions of eGFP and sTomato and vice versa separated by diverse 2A sequences have been generated. The same set of constructs has also been generated based on the constitutive $P_{GAP}$.
Figure 14:
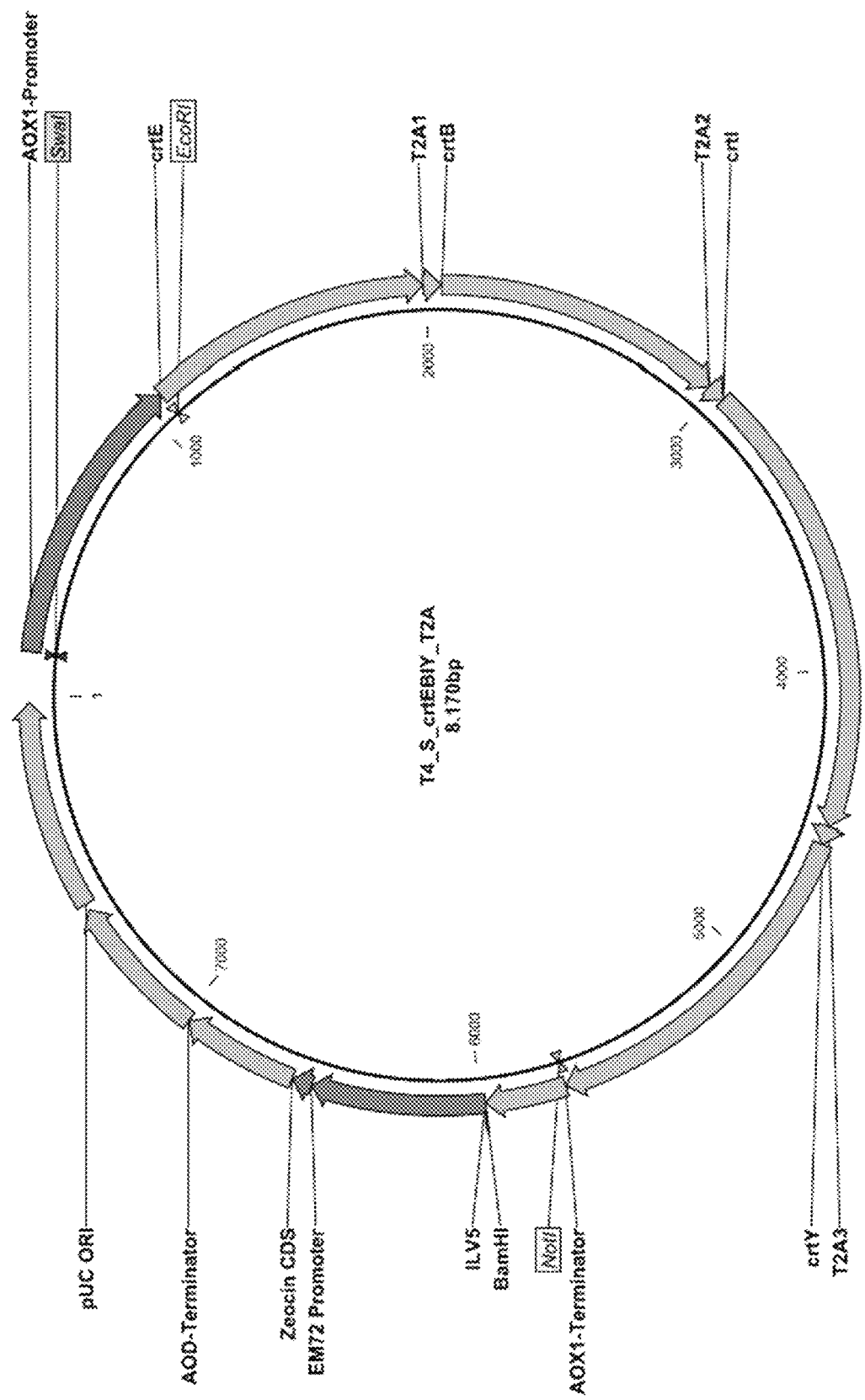
FIG. 14: Plasmid map of the polycistronic expression construct coding for the β-carotene biosynthesis pathway based on the inducible $P_{AOX1}$. The four pathway genes were fused via T2A sequences. An equivalent construct was generated based on the constitutive $P_{GAP}$.
Figure 15:
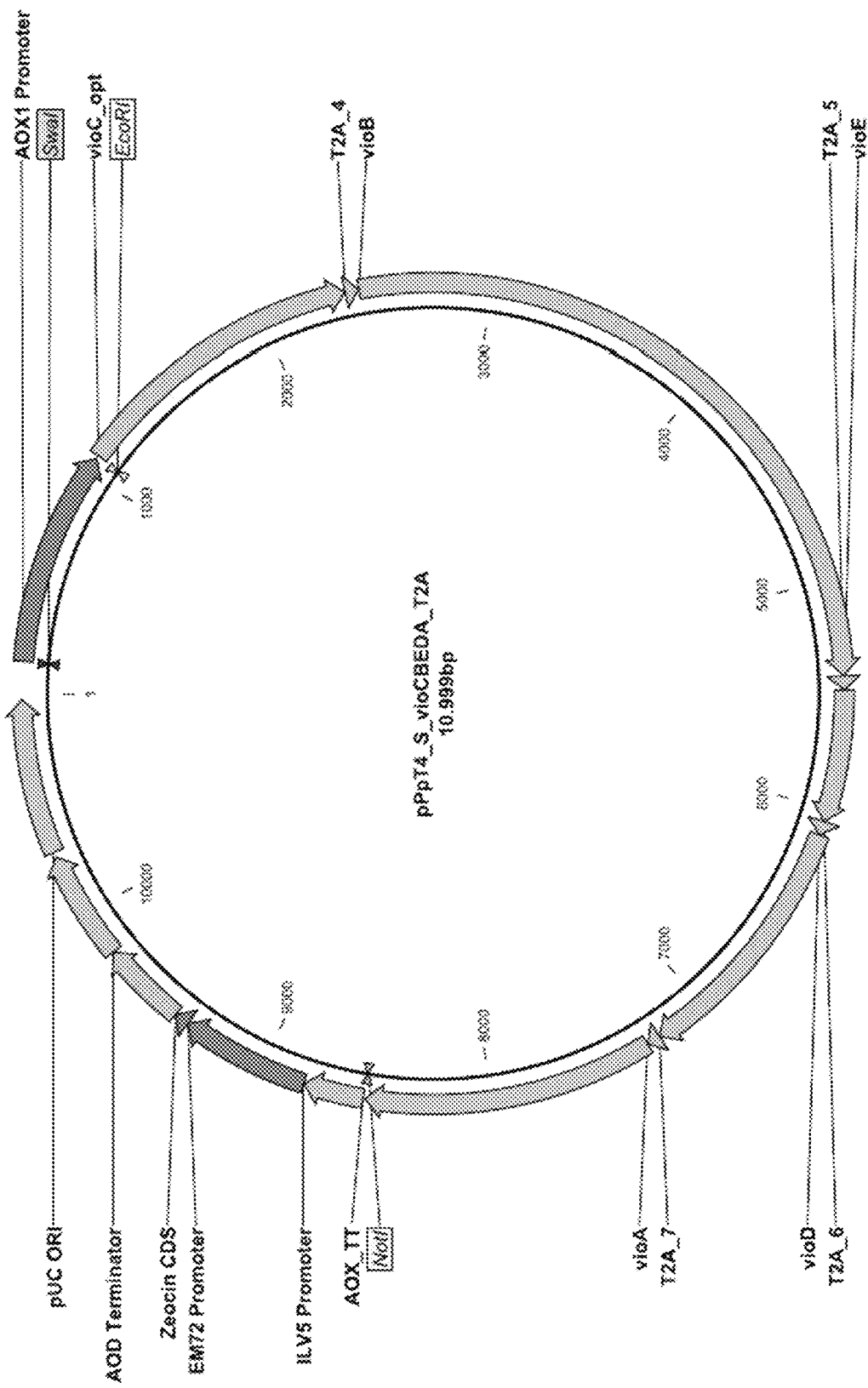
FIG. 15: Plasmid map of the polycistronic expression construct coding for the violacein biosynthesis pathway based on the inducible $P_{AOX1}$. The five pathway genes were fused via T2A sequences. An equivalent construct was generated based on the constitutive $P_{GAP}$.
Figure 16A:
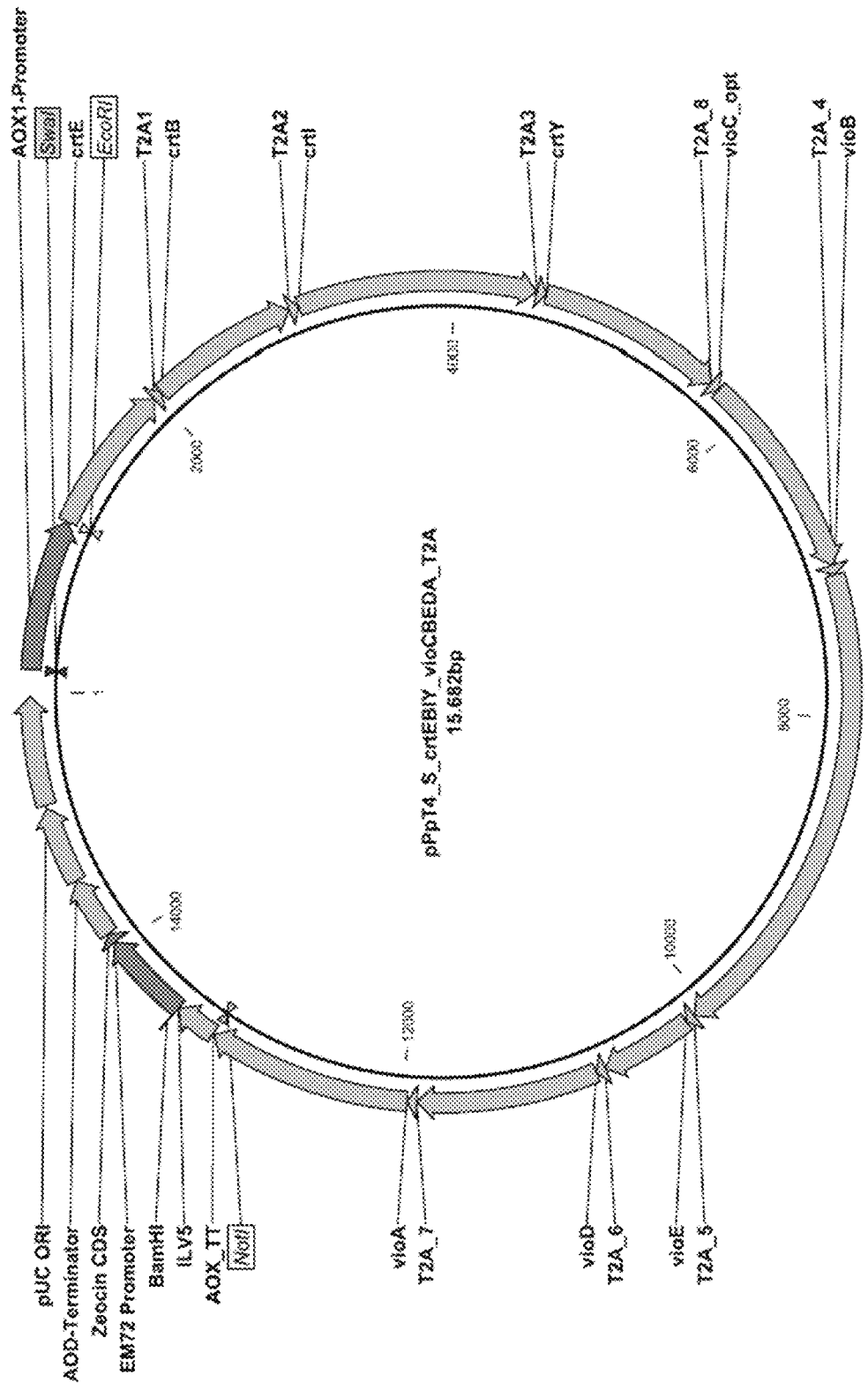
FIG. 16 A: Plasmid map of the polycistronic expression construct coding for the β-carotene and the violacein biosynthesis pathway based on the inducible $P_{AOX1}$. The nine pathway genes were fused via T2A sequences. An equivalent construct was generated based on the constitutive $P_{GAP}$.
Figure 16B:
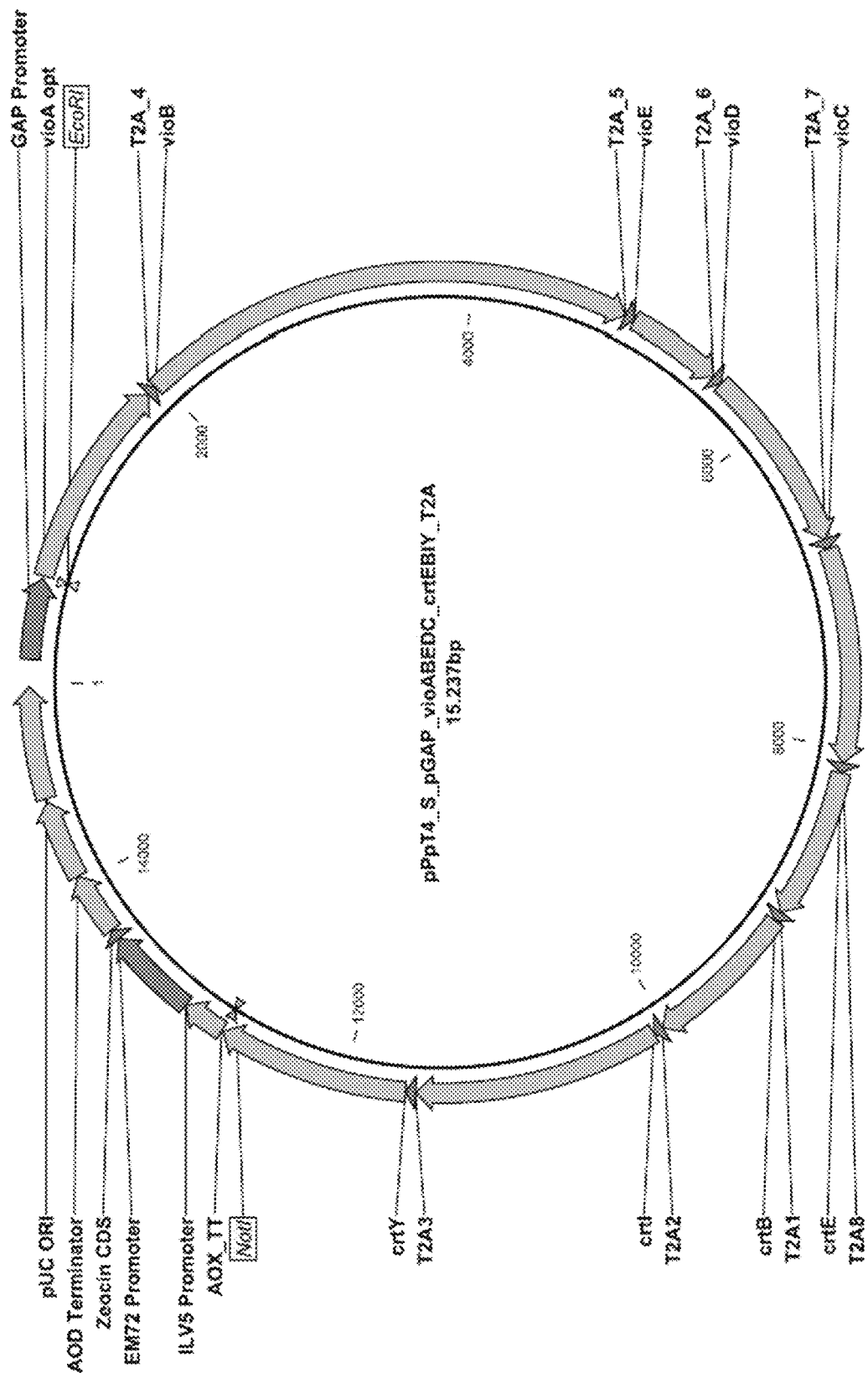
Figure 17:
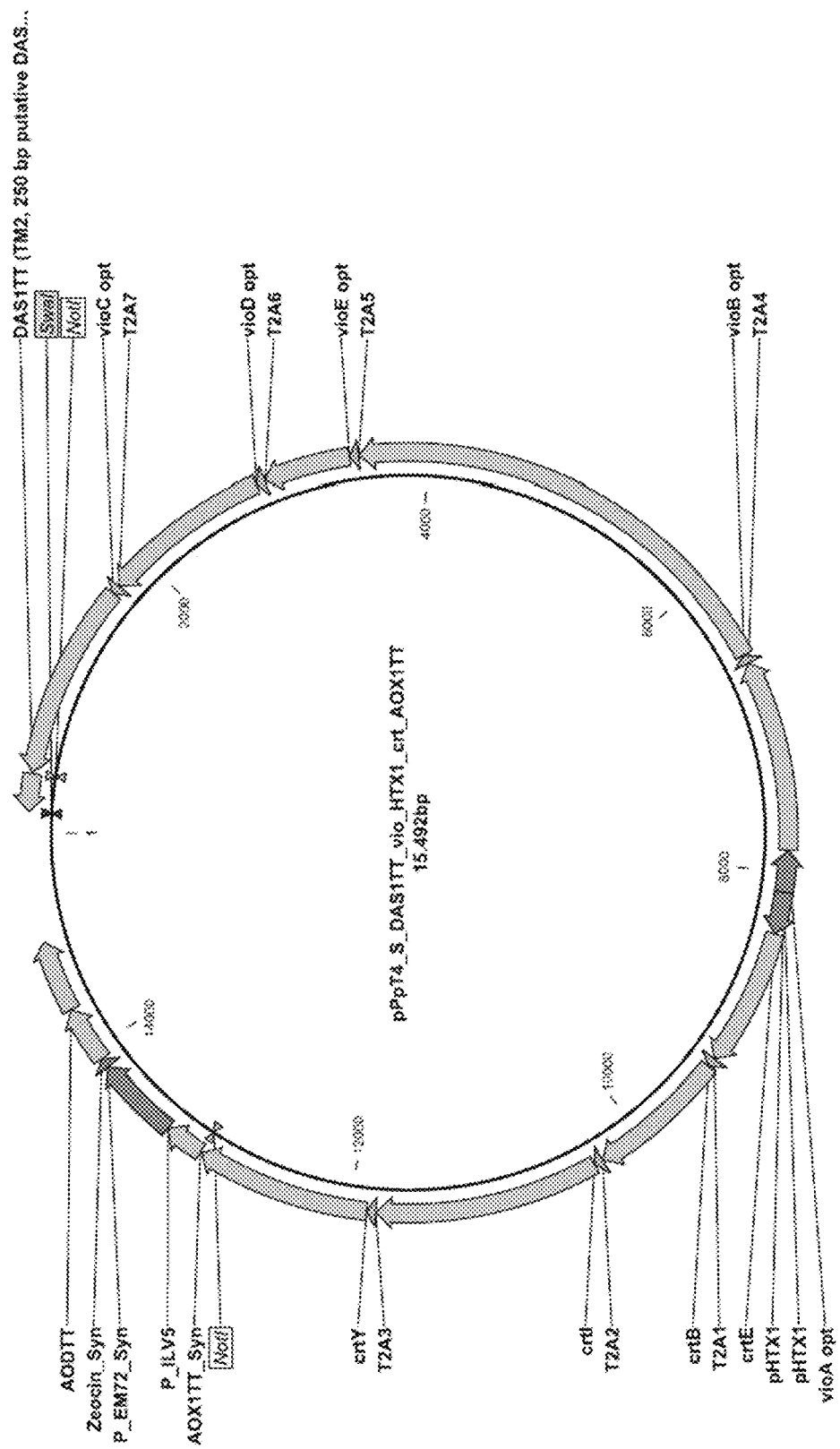
FIG. 17: Plasmid map of the polycistronic expression construct coding for the β-carotene and the violacein biosynthesis pathway based on $P_{HTX1}$. The individual pathway genes were fused via T2A sequences. An equivalent construct was generated based on the inducible $P_{BZ6}$.

Example 5—Polycistronic Pathway Expression in Combination with Bidirectional Promoters Another interesting application of 2A sequences and an alternative to tune activities of different parts of pathways constitutes their use for polycistronic pathway expression in combination with bidirectional promoters. On the one hand, this strategy allows more efficient expression of multiple genes which can lead to higher product titers. On the other hand it provides an opportunity to increase the number of coexpressed genes going significantly beyond 9-10 genes since two transcripts are generated by this short bidirectional promoter sequence. To test the general applicability of this concept expression constructs harboring the violacein and the carotenoid biosynthesis pathway in a bidirectional polycistronic format were generated as schematically depicted in FIG. 11.

Also this expression strategy results in strains successfully producing the pigments of both pathways employing a short DNA sequence driving expression in both directions. After 60 h of incubation the corresponding strains already started to turn brown (FIG. 12).

Figure 18:
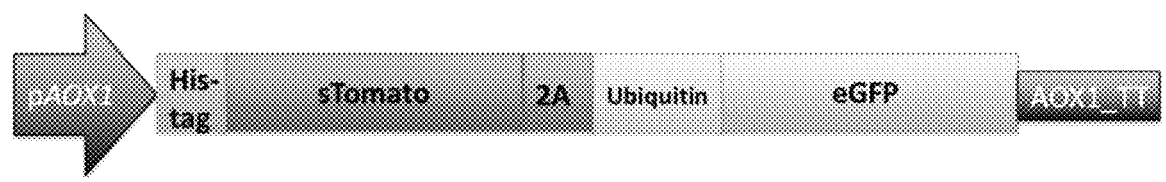
FIG. 18: Schematic representation of the polycistronic expression cassette coding for the two fluorescent proteins sTomato and eGFP carrying an additional ubiquitin linker.
Figure 19A:
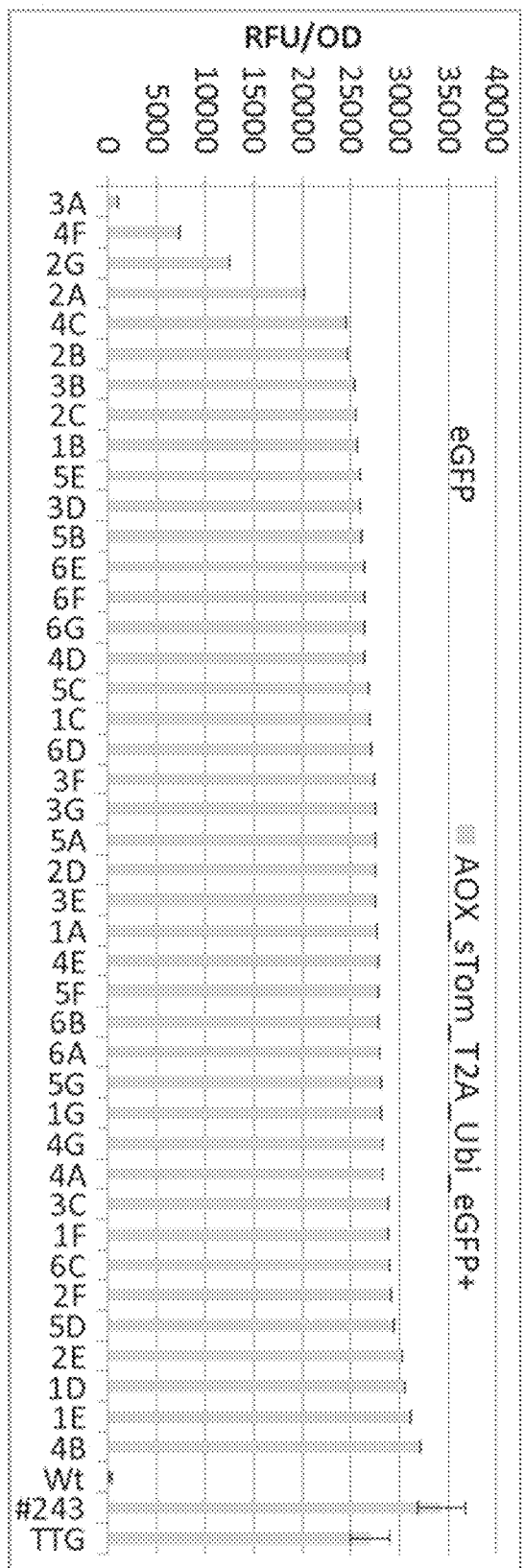
FIG. 19: eGFP and sTomato fluorescence levels obtained by coordinate expression based on 2A sequences. The screening results of the construct pPp_T4_S_sTomato_T2A_Ubiquitin_eGFP with start codon of eGFP (panel A and C) and without start codon of eGFP (panel B and D) are shown. *P. pastoris* CBS 7435 was used as negative control, strain #243 expressing eGFP and sTomato served as positive control as well as the construct pPp_T4_S_sTomato_T2A_eGFP (TTG, without ubiquitin).
Figure 19B:
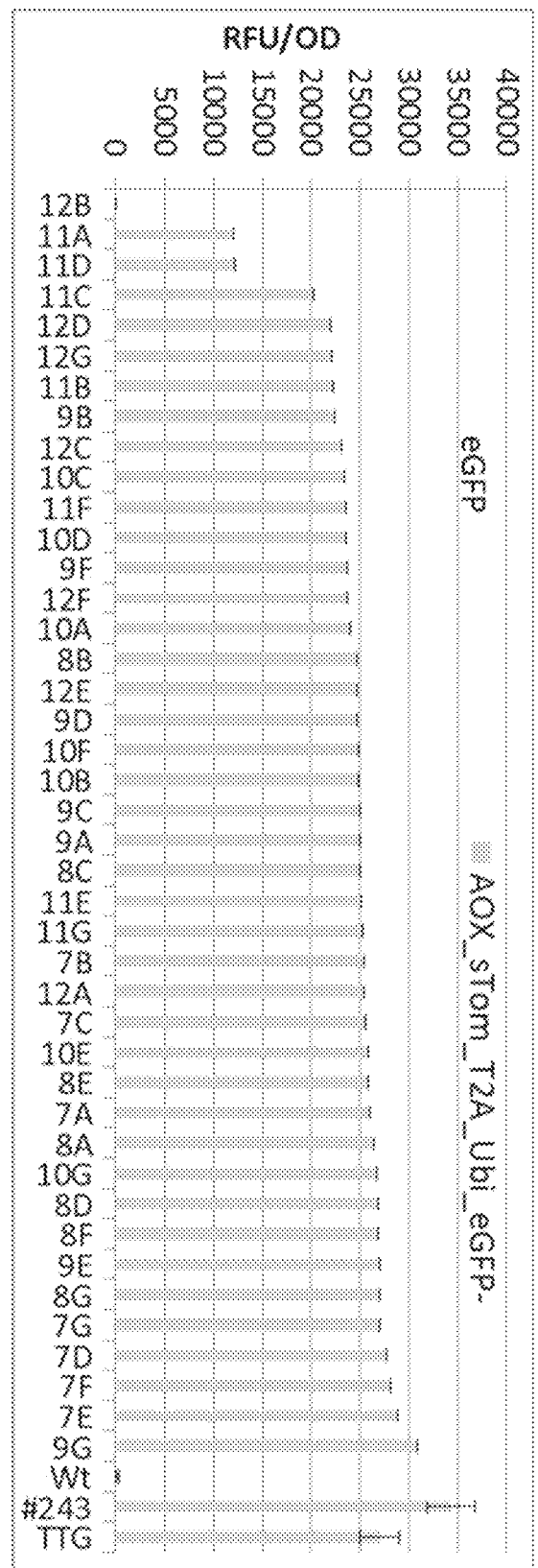
Figure 19C:
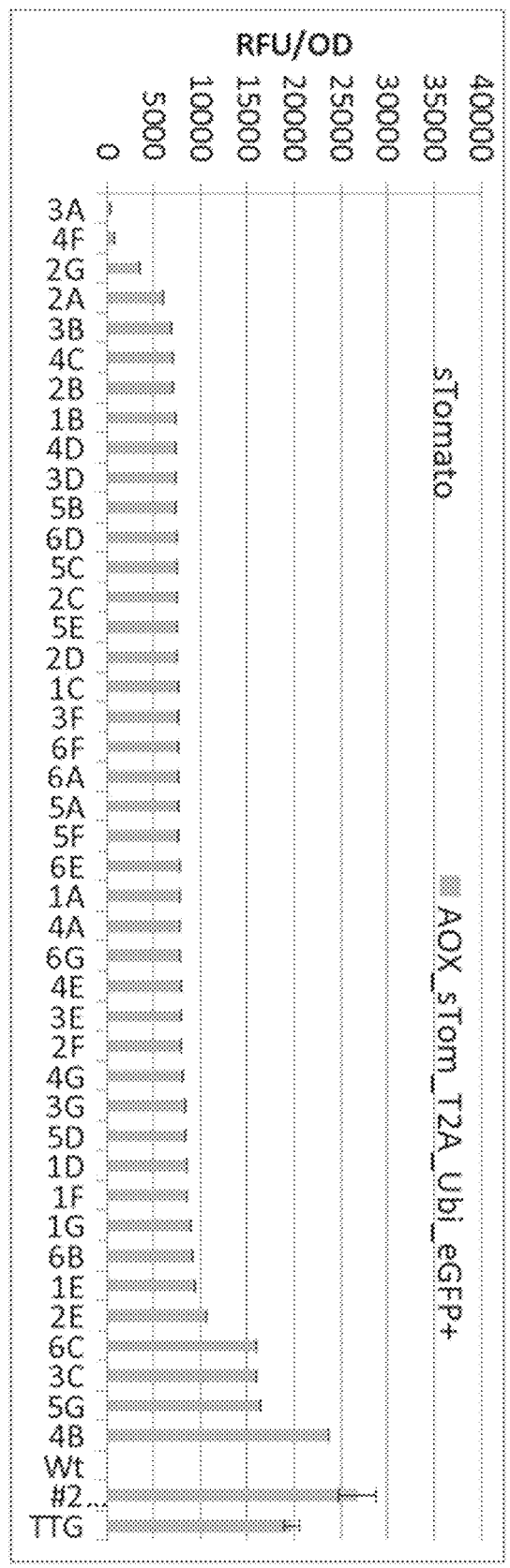
Figure 19D:
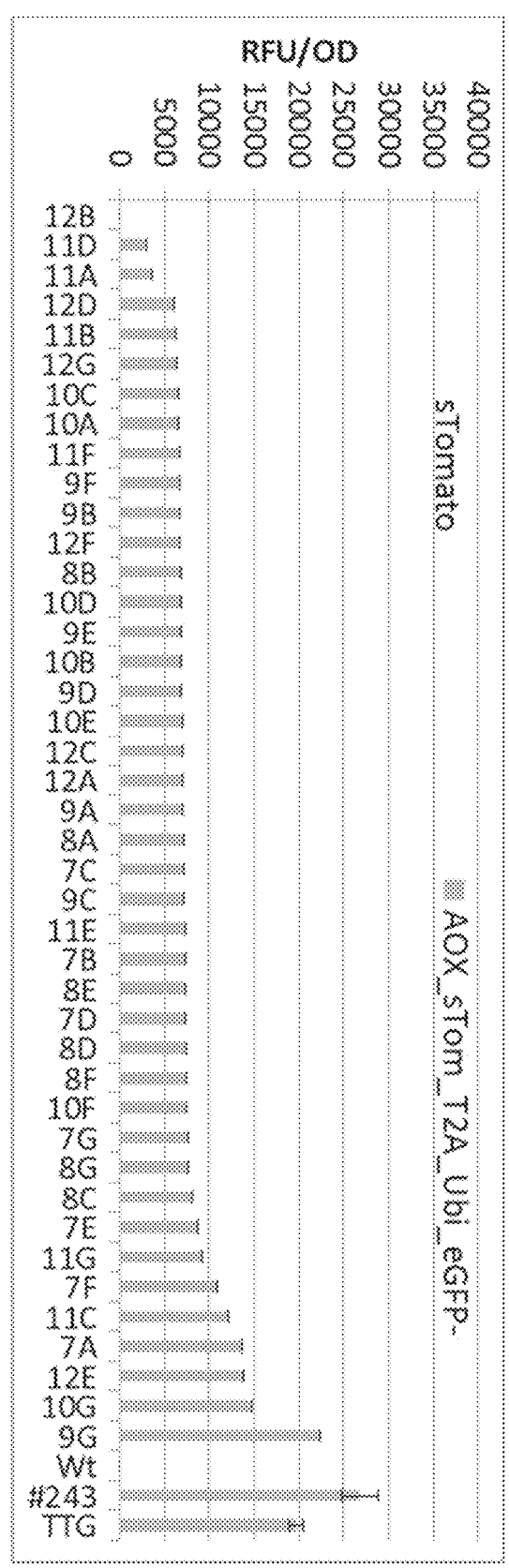

Example 6—Polycistronic Expression Constructs in Combination with an Ubiquitin Linker The C- as well as the N-terminus of the proteins located up- and downstream of the 2A sequences is modified, respectively. In case that an authentic N-terminus is required a potential strategy is to add additional sequences that are post-translationally cleaved-off. Therefore, we tested an additional ubiquitin tag as autoprotease employing an expression construct as depicted in FIG. 18. The two fluorescent proteins sTomato and eGFP (CDS with and without start codon) were fused via the T2A peptide with the ubiquitin tag intervening. The His-tag at the N-terminus of the expression construct was added to allow Western blot analysis of the resulting gene products.

The polycistronic expression construct with the additional ubiquitin linker did result in functional fluorescent proteins too. The expression levels of eGFP are in the same order of magnitude as the one obtained by a strain harboring the corresponding expression construct without ubiquitin (indicated as TTG in the landscapes of FIG. 19). However, the expression of sTomato was affected negatively, as only about 50% of the red fluorescence was detected in comparison to the unmodified construct.

Figure 20:
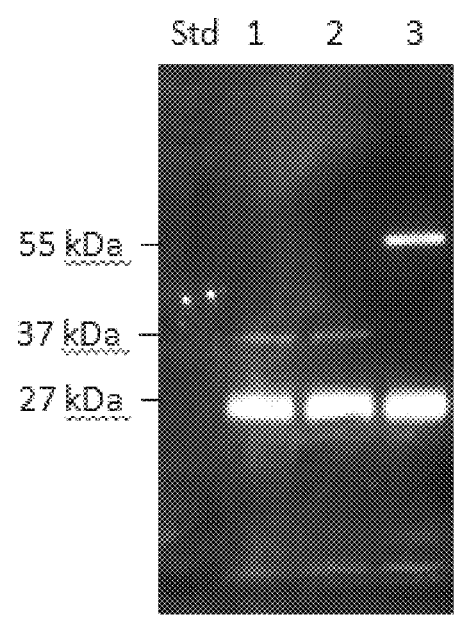
FIG. 20: Western blot analysis of crude cell lysates of *P. pastoris* strains expressing the 2A-ubiquitin constructs under the control of $P_{AOX1}$ using anti-His antibody. The expected bands of the uncleaved protein fusion (55 k kDa for sTomato_T2A_eGFP, 37 kDA for the product sTomato_T2A_Ubiquitin) and the fluorescence protein sTomato (27 kDa) are indicated. Lane 1: sTomato-T2A-ubiquitin-eGFP with start codon; 2: sTomato-T2A-ubiquitin-eGFP without start codon; 3: sTomato-T2A-eGFP 10C.
Figure 21:
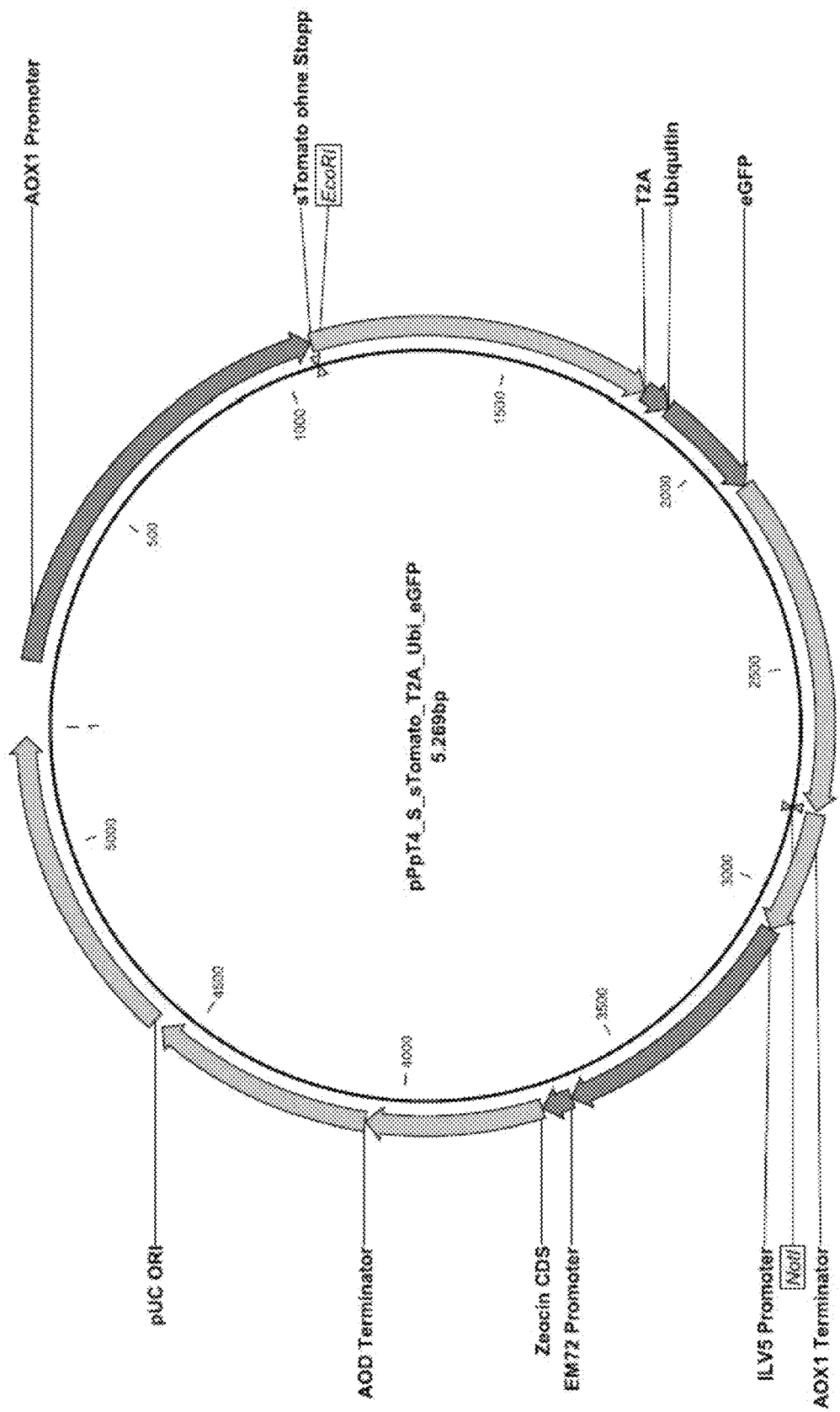
FIG. 21: Plasmid map of the polycistronic expression construct coding for the fluorescent proteins sTomato and eGFP based on the inducible $P_{AOX1}$. The sequence of ubiquitin, an autoprotease, was located between the T2A sequence and the coding sequence of eGFP with and without start codon. An equivalent construct was generated based on the constitutive $P_{GAP}$.

Western blot analysis revealed that the additional ubiquitin linker did not interfere with the T2A-mediated cleavage (FIG. 20). The predominant bands that were observed correspond to the cleaved His-tagged sTomato (~27 kDa). A band corresponding to the full length gene fusion product (i.e. sTomato_eGFP) was only observed for the polycistronic expression construct without ubiquitin tag (FIG. 20, lane 3). When ubiquitin was included, a smaller band was detected that would match the fluorescent protein sTomato carrying a C-terminal extension consisting of the 2A peptide and ubiquitin.

In addition, MS-analysis revealed that the resulting eGFP protein did not contain the 2A derived proline, but the natural N-terminus (methionine was not present independent of the presence of the start ATG).

Polycistronic Expression of a Five-gene Pathway in *S. cerevisiae*

The violacein pathway consisting of five enzymatic steps was also set up for polycistronic expression in the yeast *Saccharomyces cerevisiae*. Therefore, the five pathway genes were directly fused via T2A sequences (T2A4-T2A7), whereas the latter ones were exploited to act as homologous overlaps during the in vivo assembly of the final expression construct in yeast. Two constructs were generated that differ in the order of the individual pathway genes within the polycistron (vioABEDC and vioCBEDA).

Figure 22:
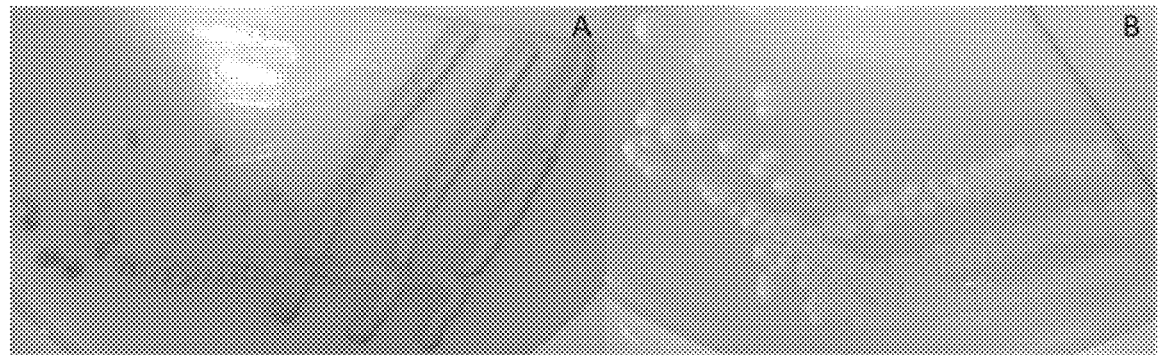
FIG. 22: *S. cerevisiae* strains producing violacein based on polycistronic expression constructs that harbor the violacein pathway in the order vioABEDC (FIG. 22A) and vioCBEDA (FIG. 22B). Functional expression of the violacein pathway is indicated by the formation of purple colored cells due to violacein formation. The order of the genes within the polycistron has a clear impact on the pathway efficiency.

The in vivo assembly of the expression constructs was successful. Again, efficient pathway expression was dependent on the order of the pathway genes within the polycistron. Strains carrying the construct in which the vio genes were placed in the order vioABEDC turned purple after 3-4 days due to the accumulation of the colored pathway end product violacein. Swapping the positions of the genes vioA and vio C, i.e. vioCBEDA, resulted in strains that did not develop a colored phenotype (see FIG. 22).

CONCLUSIONS

We have successfully shown for the first time the polycistronic expression of multiple (>2) genes based on viral 2A sequences in the methylotrophic yeast *P. pastoris*. The 2A sequences of the Thosea asigna virus (T2A) and of the porcine teschovirus-1 (P2A) were identified to efficiently mediate the production of individual proteins from a single transcript. Consequently, 2A sequences were exploited to express natural multi-gene pathways: functional pathways consisting of up to 9 enzymes were demonstrated in this study. The employment of 2A sequences for pathway generation allows a compact design and optimization of the expression construct which can be assembled more rapidly and including more genes than classical cloning strategies. Balancing individual activities along the pathway can be obtained by changing the order of peptide coding sequences on the expression construct and the repeated use of individual protein coding subsequences. In addition, the resulting expression strains exhibit an improved genetic stability in comparison to strains that are based on co-expression constructs harbouring each pathway gene under the separate control of repetitive regulatory elements. As strain stability is a crucial property for industrial applications, 2A sequences represent a valuable strategy to obtain stable production strains. In addition, 2A sequences in combination with bidirectional promoters offers further possibilities for the generation of very large homologous, heterologous and synthetic pathways.

REFERENCES

[1] Zhu, T., Guo, M., Sun, C., Qian, J., et al., A systematical investigation on the genetic stability of multi-copy *Pichia pastoris* strains. *Biotechnol. Lett.* 2009, 3, 679-84, DOI: 10.1007/s10529-009-9917-4.

[2] Ryan, M. D., King, a M., Thomas, G. P., Cleavage of foot-and-mouth disease virus polyprotein is mediated by residues located within a 19 amino acid sequence. *J. Gen. Virol.* 1991, 72 (Pt 11, 2727-32.

[3] Donnelly, M. L., Luke, G., Mehrotra, a, Li, X., et al, Analysis of the aphthovirus 2A/2B polyprotein "cleavage" mechanism indicates not a proteolytic reaction, but a novel translational effect: a putative ribosomal "skip". *J. Gen. Virol.* 2001, 82, 1013-25.

[4] Park, M., Kang, K., Park, S., Kim, Y. S., et al, Expression of serotonin derivative synthetic genes on a single self-processing polypeptide and the production of serotonin derivatives in microbes. *App. Microbiol Biotechnol.* 2008, 81, 43-9, DOI: 10.1007/s00253-008-1634-8.

[5] Beekwilder, J., van Rossum, H. M., Koopman, F., Sonntag, F., et al, Polycistronic expression of a β-carotene biosynthetic pathway in *Saccharomyces cerevisiae* coupled to β-ionone production. *J. Biotechnol.* 2014, 1-10, DOI: 10.1016/j.jbiotec.2013.12.016.

[6] Sun, Y.-F., Lin, Y., Zhang, J.-H., Zheng, S.-P., et al., Double *Candida antarctica* lipase B codisplay on *Pichia pastoris* cell surface based on a self-processing foot-and-mouth disease virus 2A peptide. *Appl. Microbiol. Biotechnol.* 2012, 96, 1539-50, DOI: 10.1007/s00253-012-4264-0.

[7] Wang, S., Yao, Q., Tao, J., Qiao, Y., et al., Co-ordinate expression of glycine betaine synthesis genes linked by the FMDV 2A region in a single open reading frame in *Pichia pastoris*. *App. Microbiol Biotechnol.* 2007, 77, 891-9, DOI: 10.1007/s00253-007-1222-3.

[8] Roongsawang, N., Promdonkoy, P., Wongwanichpokhin, M., Sornlake, W., et al, Coexpression of fungal phytase and xylanase utilizing the cis-acting hydrolase element in *Pichia pastoris*. *FEMS Yeast Res.* 2010, 10, 909-16, DOI: 10.1111/j.1567-1364.2010.00669.x.

[9] Szymczak, A. L., Workman, C. J., Wang, Y., Vignali, K. M., et al, Correction of multi-gene deficiency in vivo using a single "self-cleaving" 2A peptide-based retroviral vector. *Nat. Biotechnol.* 2004, 22, 589-94, DOI: 10.1038/nbt957.

[10] Näätsaari, L., Mistlberger, B., Ruth, C., Hajek, T., et al, Deletion of the *Pichia pastoris* KU70 Homologue Facilitates Platform Strain Generation for Gene Expression and Synthetic Biology. *PLoS One.* 2012, 7 DOI: 10.1371/journal.pone.0039720.

[11] Gibson, D., Young, L., Chuang, R., Venter, J., et al., Enzymatic assembly of DNA molecules up to several hundred kilobases. *Nat Methods.* 2009, 6, 343-5, DOI: 10.1038/nmeth.1318.

[12] Lin-Cereghino, J., Wong, W. W., Xiong, S., Giang, W., et al, Condensed protocol for competent cell preparation and transformation of the methylotrophic yeast *Pichia pastoris*. *Biotechniques.* 2005, 38, 44, 46, 48.

[13] Weis, R., Luiten, R., Skranc, W., Schwab, H., et al, Reliable high-throughput screening with *Pichia pastoris* by limiting yeast cell death phenomena. *FEMS Yeast Res.* 2004, 5, 179-89, DOI: 10.1016/j.femsyr.2004.06.016.

[14] Araya-Garay, J. M., Feijoo-Siota, L., Rosa-dos-Santos, F., Veiga-Crespo, P., et al., Construction of new *Pichia pastoris* X-33 strains for production of lycopene and β-carotene. *Appl. Microbiol. Biotechnol.* 2012, 93, 2483-92, DOI: 10.1007/s00253-011-3764-7.

[15] Unkles, S., Valiante, V., Mattern, D., Brakhage, A., Synthetic Biology Tools for Bioprospecting of Natural Products in Eukaryotes. *Chem Biol.* 2014, 21, 502-8, DOI: 10.1016/j.chembiol.2014.02.010.

[16] Yu-Ju Lin, Li-Hsin Huang, Ching-Tsan Huang, Enhancement of Heterologous Gene Expression in Flammulina velutipes Using Polycistronic Vectors Containing a Viral 2A Cleavage Sequence. *PLoS One.* 2013; 8(3): e59099. Published online 2013 Mar. 14.

[17] Radcliffe P A and Mitrophanous K A, Multiple gene products from a single vector self-cleaving 2A peptides. *Gene Therapy* 2004; 11(23): 1673-1674.

[18] De Felipe P et al., Co-translational, intraribosomal cleavage of polypeptides by the foot-and-mouth disease virus 2A peptide, *Journal of Biological Chemistry,* 2003; 278(13): 11441-11448.

[19] Hecht K., Bailey, J E., Minas W., Polycistronic gene expression in yeast versus cryptic promoter elements, *FEMS Yeast Research,* 2002; 2(2), 215-224.

The invention claimed is:

1. A recombinant polycistronic expression construct for expression of multiple genes in a yeast cell, consecutively comprising in the 5' to 3' orientation,
   a. a promoter operable in said yeast cell, and
   b. at least five genes of interest, each of which is separated by a 2A sequence, wherein at least one 2A sequence comprises one of SEQ ID Nos. 1-10.

2. The polycistronic expression construct according to claim 1, comprising at least nine genes of interest, each of which is separated by a 2A sequence.

3. The polycistronic expression construct according to claim 1, wherein said promoter is a bidirectional promoter.

4. The polycistronic expression construct according to claim 1, further comprising a His-tag encoding sequence inserted between the promoter and the adjacent gene of interest.

5. The polycistronic expression construct according to claim 1, wherein at least one 2A sequence is selected from the group consisting of porcine teschovirus-1, *Thosea asigna* virus, foot-and-mouth-disease virus, and equine rhinitis A virus (ERAV).

6. The polycistronic expression construct according to claim 1, wherein at least one 2A sequence encodes a polypeptide selected from the group consisting of SEQ ID NO.11-13.

7. The polycistronic expression construct according to claim 1, wherein each 2A sequence is an identical sequence.

8. The polycistronic expression construct according to claim 1, wherein the alignment of the at least five genes is optimized.

9. The recombinant polycistronic expression construct of claim 1, further comprising a termination signal.

10. The polycistronic expression construct according to claim 1, wherein each 2A sequence comprises a sequence selected from SEQ ID Nos. 1-10.

11. The polycistronic expression construct according to claim 1, wherein each 2A sequence is a different sequence.

12. Yeast cell containing a polycistronic expression construct according to claim 1.

13. A method for producing a transgenic yeast cell, wherein a yeast cell is transformed with the polycistronic expression construct according to claim 1.

14. A method of producing multiple polypeptides in a yeast cell comprising the steps of
   a. transforming the yeast cell with an expression construct according to claim 1,
   b. culturing the yeast cell under conditions sufficient to express the expression construct comprising the genes of interest, and
   c. isolating polypeptides of interest expressed from the genes of interest.

15. A method for producing a compound comprising culturing a yeast cell comprising a polycistronic expression construct according to claim 1 under conditions such that the compound is produced.

16. A recombinant polycistronic expression construct for expression of multiple genes in a yeast cell, consecutively comprising in the 5' to 3' orientation
   a. at least two or more genes of interest, each of which is separated by a 2A sequence,
   b. a bi-directional promoter,
   c. at least two or more genes of interest, each of which is separated by a 2A sequence,
   wherein the recombinant polycistronic expression construct comprises at least five genes of interest, and wherein at least one 2A sequence comprises one of SEQ ID Nos. 1-10.

17. The recombinant polycistronic expression construct of claim 16, further comprising a termination signal 5' to the at least two or more genes of interests of (a).

18. The recombinant polycistronic expression construct of claim 16, further comprising a termination signal 3' to the at least two or more genes of interests of (c).

* * * * *

SEQUENCE LISTING

<160> NUMBER OF SEQ ID NOS: 99

<210> SEQ ID NO 1
<211> LENGTH: 60
<212> TYPE: DNA
<213> ORGANISM: Artificial Sequence
<220> FEATURE:
<223> OTHER INFORMATION: T2A1

<400> SEQUENCE: 1
agagctgagg gtagaggttc tttgcttact tgcggtgacg ttgaggaaaa cccaggtcca    60

<210> SEQ ID NO 2
<211> LENGTH: 60
<212> TYPE: DNA
<213> ORGANISM: Artificial Sequence
<220> FEATURE:
<223> OTHER INFORMATION: T2A2

<400> SEQUENCE: 2
cgtgccgaag gacgtggatc cctttgacc tgcggagatg tcgaagagaa tcctggacct    60

<210> SEQ ID NO 3
<211> LENGTH: 60
<212> TYPE: DNA
<213> ORGANISM: Artificial Sequence
<220> FEATURE:
<223> OTHER INFORMATION: T2A3

<400> SEQUENCE: 3
agagcagaag gtcgtggctc attgctgact tgtggcgacg tggaggaaaa tcccggacca    60

<210> SEQ ID NO 4
<211> LENGTH: 60
<212> TYPE: DNA
<213> ORGANISM: Artificial Sequence
<220> FEATURE:
<223> OTHER INFORMATION: T2A4

<400> SEQUENCE: 4
cgtgcagagg gccgtggttc cttacttacc tgcggtgatg tggaagaaaa tccaggaccc    60

<210> SEQ ID NO 5
<211> LENGTH: 60
<212> TYPE: DNA
<213> ORGANISM: Artificial Sequence
<220> FEATURE:
<223> OTHER INFORMATION: T2A5

<400> SEQUENCE: 5
cgtgccgagg gtaggggatc acttcttaca tgtggagacg tcgaggagaa ccctggtcca    60

<210> SEQ ID NO 6
<211> LENGTH: 60
<212> TYPE: DNA
<213> ORGANISM: Artificial Sequence
<220> FEATURE:
<223> OTHER INFORMATION: T2A6

<400> SEQUENCE: 6
agagctgaag gaaggggttc cctgttaacg tgtggcgatg ttgaagagaa ccccggtcct    60

<210> SEQ ID NO 7
<211> LENGTH: 60
<212> TYPE: DNA
<213> ORGANISM: Artificial Sequence

<220> FEATURE:
<223> OTHER INFORMATION: T2A7

<400> SEQUENCE: 7
agggcagaag gcagaggatc tctgttgact tgtggtgatg tagaggagaa tcccggccca    60

<210> SEQ ID NO 8
<211> LENGTH: 60
<212> TYPE: DNA
<213> ORGANISM: Artificial Sequence
<220> FEATURE:
<223> OTHER INFORMATION: T2A8

<400> SEQUENCE: 8
agggcggagg ggagaggctc tcttttaact tgtggagatg tggaagagaa cccaggccct    60

<210> SEQ ID NO 9
<211> LENGTH: 57
<212> TYPE: DNA
<213> ORGANISM: Artificial Sequence
<220> FEATURE:
<223> OTHER INFORMATION: P2A

<400> SEQUENCE: 9
gctactaact tctctttgct taagcaagct ggtgacgttg aggaaaaccc aggtcca    57

<210> SEQ ID NO 10
<211> LENGTH: 60
<212> TYPE: DNA
<213> ORGANISM: Artificial Sequence
<220> FEATURE:
<223> OTHER INFORMATION: FMDV2A

<400> SEQUENCE: 10
caattgctta acttcgactt attgaagctt gctggtgacg ttgagtctaa cccaggtcca    60

<210> SEQ ID NO 11
<211> LENGTH: 20
<212> TYPE: PRT
<213> ORGANISM: Artificial Sequence
<220> FEATURE:
<223> OTHER INFORMATION: FMDV2A

<400> SEQUENCE: 11

Gln Leu Leu Asn Phe Asp Leu Leu Lys Leu Ala Gly Asp Val Glu Ser
1               5                   10                  15

Asn Pro Gly Pro
            20

<210> SEQ ID NO 12
<211> LENGTH: 20
<212> TYPE: PRT
<213> ORGANISM: Artificial Sequence
<220> FEATURE:
<223> OTHER INFORMATION: T2A

<400> SEQUENCE: 12

Arg Ala Glu Gly Arg Gly Ser Leu Leu Thr Cys Gly Asp Val Glu Glu
1               5                   10                  15

Asn Pro Gly Pro
            20

<210> SEQ ID NO 13
<211> LENGTH: 19
<212> TYPE: PRT

```
<213> ORGANISM: Artificial Sequence
<220> FEATURE:
<223> OTHER INFORMATION: P2A

<400> SEQUENCE: 13

Ala Thr Asn Phe Ser Leu Leu Lys Gln Ala Gly Asp Val Glu Glu Asn
1               5                   10                  15

Pro Gly Pro

<210> SEQ ID NO 14
<211> LENGTH: 20
<212> TYPE: PRT
<213> ORGANISM: Artificial Sequence
<220> FEATURE:
<223> OTHER INFORMATION: F2A

<400> SEQUENCE: 14

Gln Leu Leu Asn Phe Asp Leu Leu Lys Leu Ala Gly Asp Val Glu Ser
1               5                   10                  15

Asn Pro Gly Ala
            20

<210> SEQ ID NO 15
<211> LENGTH: 48
<212> TYPE: DNA
<213> ORGANISM: Artificial Sequence
<220> FEATURE:
<223> OTHER INFORMATION: eGFP_EcoRI_fwd

<400> SEQUENCE: 15
aaatgaattc cgaaacgatg gctagcaaag gagaagaact tttcactg               48

<210> SEQ ID NO 16
<211> LENGTH: 92
<212> TYPE: DNA
<213> ORGANISM: Artificial Sequence
<220> FEATURE:
<223> OTHER INFORMATION: eGFP_FMDV2A_rev

<400> SEQUENCE: 16
tggacctggg ttagactcaa cgtcaccagc aagcttcaat aagtcgaagt taagcaattg     60
cttgtacaat tcatccatgc catgtgtaat cc                                   92

<210> SEQ ID NO 17
<211> LENGTH: 89
<212> TYPE: DNA
<213> ORGANISM: Artificial Sequence
<220> FEATURE:
<223> OTHER INFORMATION: eGFP_P2A_rev

<400> SEQUENCE: 17
tggacctggg ttttcctcaa cgtcaccagc ttgcttaagc aaagagaagt tagtagcctt     60
gtacaattca tccatgccat gtgtaatcc                                       89

<210> SEQ ID NO 18
<211> LENGTH: 92
<212> TYPE: DNA
<213> ORGANISM: Artificial Sequence
<220> FEATURE:
<223> OTHER INFORMATION: eGFP_T2A_rev

<400> SEQUENCE: 18
tggacctggg ttttcctcaa cgtcaccgca agtaagcaaa gaacctctac cctcagctct     60
```

```
cttgtacaat tcatccatgc catgtgtaat cc                                  92

<210> SEQ ID NO 19
<211> LENGTH: 93
<212> TYPE: DNA
<213> ORGANISM: Artificial Sequence
<220> FEATURE:
<223> OTHER INFORMATION: sTomato_FMDV2A_fwd_mit Startcodon

<400> SEQUENCE: 19
caattgctta acttcgactt attgaagctt gctggtgacg ttgagtctaa cccaggtcca    60
atggtttcta agggtgagga agttatcaag gag                                 93

<210> SEQ ID NO 20
<211> LENGTH: 96
<212> TYPE: DNA
<213> ORGANISM: Artificial Sequence
<220> FEATURE:
<223> OTHER INFORMATION: sTomato_FMDV2A_fwd_ohne Startcodon

<400> SEQUENCE: 20
caattgctta acttcgactt attgaagctt gctggtgacg ttgagtctaa cccaggtcca    60
gtttctaagg gtgaggaagt tatcaaggag ttcatg                              96

<210> SEQ ID NO 21
<211> LENGTH: 93
<212> TYPE: DNA
<213> ORGANISM: Artificial Sequence
<220> FEATURE:
<223> OTHER INFORMATION: sTomato_P2A_fwd

<400> SEQUENCE: 21
gctactaact tctctttgct taagcaagct ggtgacgttg aggaaaaccc aggtccagtt    60
tctaagggtg aggaagttat caaggagttc atg                                 93

<210> SEQ ID NO 22
<211> LENGTH: 96
<212> TYPE: DNA
<213> ORGANISM: Artificial Sequence
<220> FEATURE:
<223> OTHER INFORMATION: sTomato_T2A_fwd

<400> SEQUENCE: 22
agagctgagg gtagaggttc tttgcttact tgcggtgacg ttgaggaaaa cccaggtcca    60
gtttctaagg gtgaggaagt tatcaaggag ttcatg                              96

<210> SEQ ID NO 23
<211> LENGTH: 49
<212> TYPE: DNA
<213> ORGANISM: Artificial Sequence
<220> FEATURE:
<223> OTHER INFORMATION: sTomato_NotI_rev

<400> SEQUENCE: 23
tattgcggcc gcttacttat aaagctcgtc cataccgtac aagaacaag                49

<210> SEQ ID NO 24
<211> LENGTH: 50
<212> TYPE: DNA
<213> ORGANISM: Artificial Sequence
<220> FEATURE:
<223> OTHER INFORMATION: sTomato_EcoRI_fwd

<400> SEQUENCE: 24
```
aaatgaattc cgaaacgatg gtttctaagg gtgaggaagt tatcaaggag         50

<210> SEQ ID NO 25
<211> LENGTH: 94
<212> TYPE: DNA
<213> ORGANISM: Artificial Sequence
<220> FEATURE:
<223> OTHER INFORMATION: sTomato_FMDV2A_rev

<400> SEQUENCE: 25
tggacctggg ttagactcaa cgtcaccagc aagcttcaat aagtcgaagt taagcaattg    60
cttataaagc tcgtccatac cgtacaagaa caag                               94

<210> SEQ ID NO 26
<211> LENGTH: 91
<212> TYPE: DNA
<213> ORGANISM: Artificial Sequence
<220> FEATURE:
<223> OTHER INFORMATION: sTomato_P2A_rev

<400> SEQUENCE: 26
tggacctggg ttttcctcaa cgtcaccagc ttgcttaagc aaagagaagt tagtagcctt    60
ataaagctcg tccataccgt acaagaacaa g                                  91

<210> SEQ ID NO 27
<211> LENGTH: 94
<212> TYPE: DNA
<213> ORGANISM: Artificial Sequence
<220> FEATURE:
<223> OTHER INFORMATION: sTomato_T2A_rev

<400> SEQUENCE: 27
tggacctggg ttttcctcaa cgtcaccgca agtaagcaaa gaacctctac cctcagctct    60
cttataaagc tcgtccatac cgtacaagaa caag                               94

<210> SEQ ID NO 28
<211> LENGTH: 91
<212> TYPE: DNA
<213> ORGANISM: Artificial Sequence
<220> FEATURE:
<223> OTHER INFORMATION: eGFP_ FMDV2A_fwd

<400> SEQUENCE: 28
caattgctta acttcgactt attgaagctt gctggtgacg ttgagtctaa cccaggtcca    60
gctagcaaag gagaagaact tttcactgga g                                  91

<210> SEQ ID NO 29
<211> LENGTH: 88
<212> TYPE: DNA
<213> ORGANISM: Artificial Sequence
<220> FEATURE:
<223> OTHER INFORMATION: eGFP_P2A_fwd

<400> SEQUENCE: 29
gctactaact tctctttgct taagcaagct ggtgacgttg aggaaaaccc aggtccagct    60
agcaaaggag aagaactttt cactggag                                      88

<210> SEQ ID NO 30
<211> LENGTH: 91
<212> TYPE: DNA
<213> ORGANISM: Artificial Sequence
<220> FEATURE:

<223> OTHER INFORMATION: eGFP_T2A_fwd

<400> SEQUENCE: 30
agagctgagg gtagaggttc tttgcttact tgcggtgacg ttgaggaaaa cccaggtcca    60
gctagcaaag gagaagaact tttcactgga g    91

<210> SEQ ID NO 31
<211> LENGTH: 47
<212> TYPE: DNA
<213> ORGANISM: Artificial Sequence
<220> FEATURE:
<223> OTHER INFORMATION: eGFP_NotI_rev

<400> SEQUENCE: 31
tattgcggcc gcttacttgt acaattcatc catgccatgt gtaatcc    47

<210> SEQ ID NO 32
<211> LENGTH: 79
<212> TYPE: DNA
<213> ORGANISM: Artificial Sequence
<220> FEATURE:
<223> OTHER INFORMATION: sTomato_Gibson_rev

<400> SEQUENCE: 32
ctctcaggca aatggcattc tgacatcctc ttgagcggcc gcttacttat aaagctcgtc    60
cataccgtac aagaacaag    79

<210> SEQ ID NO 33
<211> LENGTH: 77
<212> TYPE: DNA
<213> ORGANISM: Artificial Sequence
<220> FEATURE:
<223> OTHER INFORMATION: eGFP_Gibson_rev

<400> SEQUENCE: 33
ctctcaggca aatggcattc tgacatcctc ttgagcggcc gcttacttgt acaattcatc    60
catgccatgt gtaatcc    77

<210> SEQ ID NO 34
<211> LENGTH: 103
<212> TYPE: DNA
<213> ORGANISM: Artificial Sequence
<220> FEATURE:
<223> OTHER INFORMATION: eGFP_AOX_Gibson_His_fwd

<400> SEQUENCE: 34
acgacaactt gagaagatca aaaacaact aattattgaa agaattccga acgatgcac    60 caccatcacc accatgctag caaaggagaa gaactttca ctg    103

<210> SEQ ID NO 35
<211> LENGTH: 105
<212> TYPE: DNA
<213> ORGANISM: Artificial Sequence
<220> FEATURE:
<223> OTHER INFORMATION: sTomato_AOX_Gibson_His_fwd

<400> SEQUENCE: 35
acgacaactt gagaagatca aaaacaact aattattgaa agaattccga acgatgcac    60 caccatcacc accatgtttc taagggtgag gaagttatca aggag    105

<210> SEQ ID NO 36
<211> LENGTH: 100

```
<212> TYPE: DNA
<213> ORGANISM: Artificial Sequence
<220> FEATURE:
<223> OTHER INFORMATION: eGFP_GAP_Gibson_His_fwd

<400> SEQUENCE: 36
gtccctattt caatcaattg aacaactatc aaaacacaga attccgaaac gatgcaccac      60
catcaccacc atgctagcaa aggagaagaa cttttcactg                           100

<210> SEQ ID NO 37
<211> LENGTH: 102
<212> TYPE: DNA
<213> ORGANISM: Artificial Sequence
<220> FEATURE:
<223> OTHER INFORMATION: sTomato_GAP_Gibson_His_fwd

<400> SEQUENCE: 37
gtccctattt caatcaattg aacaactatc aaaacacaga attccgaaac gatgcaccac      60
catcaccacc atgtttctaa gggtgaggaa gttatcaagg ag                        102

<210> SEQ ID NO 38
<211> LENGTH: 65
<212> TYPE: DNA
<213> ORGANISM: Artificial Sequence
<220> FEATURE:
<223> OTHER INFORMATION: pAOX1_crtE_fw

<400> SEQUENCE: 38
cgacaacttg agaagatcaa aaacaacta attattgaaa gaattccgaa acgatgacgg      60
tctgc                                                                 65

<210> SEQ ID NO 39
<211> LENGTH: 84
<212> TYPE: DNA
<213> ORGANISM: Artificial Sequence
<220> FEATURE:
<223> OTHER INFORMATION: crtE_T2A_rev

<400> SEQUENCE: 39
tggacctggg ttttcctcaa cgtcaccgca agtaagcaaa gaacctctac cctcagctct     60
actgacggca gcgagttttt tgtc                                            84

<210> SEQ ID NO 40
<211> LENGTH: 88
<212> TYPE: DNA
<213> ORGANISM: Artificial Sequence
<220> FEATURE:
<223> OTHER INFORMATION: crtB_T2A_fw

<400> SEQUENCE: 40
agagctgagg gtagaggttc tttgcttact tgcggtgacg ttgaggaaaa cccaggtcca     60
aataatccgt cgttactcaa tcatgcgg                                        88

<210> SEQ ID NO 41
<211> LENGTH: 81
<212> TYPE: DNA
<213> ORGANISM: Artificial Sequence
<220> FEATURE:
<223> OTHER INFORMATION: crtB_T2A_rev

<400> SEQUENCE: 41
aggtccagga ttctcttcga catctccgca ggtcaaaagg gatccacgtc cttcggcacg     60
```

<210> SEQ ID NO 42
<211> LENGTH: 86
<212> TYPE: DNA
<213> ORGANISM: Artificial Sequence
<220> FEATURE:
<223> OTHER INFORMATION: crtI_T2A_fw

<400> SEQUENCE: 42
cgtgccgaag gacgtggatc ccttttgacc tgcggagatg tcgaagagaa tcctggacct    60
aaaccaacta cggtaattgg tgcagg                                         86

<210> SEQ ID NO 43
<211> LENGTH: 87
<212> TYPE: DNA
<213> ORGANISM: Artificial Sequence
<220> FEATURE:
<223> OTHER INFORMATION: crtI_T2A_rev

<400> SEQUENCE: 43
tggtccggga ttttcctcca cgtcgccaca agtcagcaat gagccacgac cttctgctct    60
tatcagatcc tccagcatca aacctgc                                        87

<210> SEQ ID NO 44
<211> LENGTH: 88
<212> TYPE: DNA
<213> ORGANISM: Artificial Sequence
<220> FEATURE:
<223> OTHER INFORMATION: crtY_T2A_fw

<400> SEQUENCE: 44
agagcagaag gtcgtggctc attgctgact tgtggcgacg tggaggaaaa tcccggacca    60
caaccgcatt atgatctgat tctcgtgg                                       88

<210> SEQ ID NO 45
<211> LENGTH: 52
<212> TYPE: DNA
<213> ORGANISM: Artificial Sequence
<220> FEATURE:
<223> OTHER INFORMATION: crtY_AOX_TT_rev

<400> SEQUENCE: 45
caggcaaatg gcattctgac atcctcttga gcggccgctt aacgatgagt cg            52

<210> SEQ ID NO 46
<211> LENGTH: 63
<212> TYPE: DNA
<213> ORGANISM: Artificial Sequence
<220> FEATURE:
<223> OTHER INFORMATION: pGAP_crtE_fw

<400> SEQUENCE: 46
gtccctattt caatcaattg aacaactatc aaaacacaga attccgaaac gatgacggtc    60
tgc                                                                  63

<210> SEQ ID NO 47
<211> LENGTH: 81
<212> TYPE: DNA
<213> ORGANISM: Artificial Sequence
<220> FEATURE:
<223> OTHER INFORMATION: crtB_FMDV2A_rev

<400> SEQUENCE: 47

```
tggacctggg ttagactcaa cgtcaccagc aagcttcaat aagtcgaagt taagcaattg    60
gagcgggcgc tgccagagat g                                              81
```

<210> SEQ ID NO 48
<211> LENGTH: 86
<212> TYPE: DNA
<213> ORGANISM: Artificial Sequence
<220> FEATURE:
<223> OTHER INFORMATION: crtI_FMDV2A_fw

<400> SEQUENCE: 48

```
caattgctta acttcgactt attgaagctt gctggtgacg ttgagtctaa cccaggtcca    60
aaaccaacta cggtaattgg tgcagg                                         86
```

<210> SEQ ID NO 49
<211> LENGTH: 84
<212> TYPE: DNA
<213> ORGANISM: Artificial Sequence
<220> FEATURE:
<223> OTHER INFORMATION: crtI_P2A_rev

<400> SEQUENCE: 49

```
tggacctggg ttttcctcaa cgtcaccagc ttgcttaagc aaagagaagt tagtagctat    60
cagatcctcc agcatcaaac ctgc                                           84
```

<210> SEQ ID NO 50
<211> LENGTH: 85
<212> TYPE: DNA
<213> ORGANISM: Artificial Sequence
<220> FEATURE:
<223> OTHER INFORMATION: crtY_P2A_fw

<400> SEQUENCE: 50

```
gctactaact tctctttgct taagcaagct ggtgacgttg aggaaaaccc aggtccacaa    60
ccgcattatg atctgattct cgtgg                                          85
```

<210> SEQ ID NO 51
<211> LENGTH: 70
<212> TYPE: DNA
<213> ORGANISM: Artificial Sequence
<220> FEATURE:
<223> OTHER INFORMATION: pGAP_vioC_fw

<400> SEQUENCE: 51

```
gtccctattt caatcaattg aacaactatc aaaacacaga attccgaaac gatgaagaga    60
gctatcattg                                                           70
```

<210> SEQ ID NO 52
<211> LENGTH: 72
<212> TYPE: DNA
<213> ORGANISM: Artificial Sequence
<220> FEATURE:
<223> OTHER INFORMATION: pAOX1_vioC_fw

<400> SEQUENCE: 52

```
cgacaacttg agaagatcaa aaacaacta attattgaaa gaattccgaa acgatgaaga    60
gagctatcat tg                                                        72
```

<210> SEQ ID NO 53
<211> LENGTH: 91
<212> TYPE: DNA

<213> ORGANISM: Artificial Sequence
<220> FEATURE:
<223> OTHER INFORMATION: vioC_T2A4_rev

<400> SEQUENCE: 53
gggtcctgga ttttcttcca catcaccgca ggtaagtaag gaaccacggc cctctgcacg    60
gttaactcta ccaatcttgt accagacgtt c                                   91

<210> SEQ ID NO 54
<211> LENGTH: 91
<212> TYPE: DNA
<213> ORGANISM: Artificial Sequence
<220> FEATURE:
<223> OTHER INFORMATION: T2A4_vioB_fw

<400> SEQUENCE: 54
cgtgcagagg gccgtggttc cttacttacc tgcggtgatg tggaagaaaa tccaggaccc    60
tctattttgg acttcccaag aatccacttt c                                   91

<210> SEQ ID NO 55
<211> LENGTH: 87
<212> TYPE: DNA
<213> ORGANISM: Artificial Sequence
<220> FEATURE:
<223> OTHER INFORMATION: vioB_T2A5_rev

<400> SEQUENCE: 55
tggaccaggg ttctcctcga cgtctccaca tgtaagaagt gatcccctac cctcggcacg    60
agcttcacga gataactttc cacaagc                                        87

<210> SEQ ID NO 56
<211> LENGTH: 82
<212> TYPE: DNA
<213> ORGANISM: Artificial Sequence
<220> FEATURE:
<223> OTHER INFORMATION: T2A5_vioE_fw

<400> SEQUENCE: 56
cgtgccgagg gtaggggatc acttcttaca tgtggagacg tcgaggagaa ccctggtcca    60
gaaaaccgtg agccaccttt gc                                             82

<210> SEQ ID NO 57
<211> LENGTH: 82
<212> TYPE: DNA
<213> ORGANISM: Artificial Sequence
<220> FEATURE:
<223> OTHER INFORMATION: vioE_T2A6_rev

<400> SEQUENCE: 57
aggaccgggg ttctcttcaa catcgccaca cgttaacagg gaacccct tc cttcagctct    60 tctcttagcg gcgaagacag cg                                             82

<210> SEQ ID NO 58
<211> LENGTH: 85
<212> TYPE: DNA
<213> ORGANISM: Artificial Sequence
<220> FEATURE:
<223> OTHER INFORMATION: T2A6_vioD_fw

<400> SEQUENCE: 58
agagctgaag gaaggggttc cctgttaacg tgtggcgatg ttgaagagaa ccccggtcct    60
aagatccttg tgattggtgc aggac                                          85

<210> SEQ ID NO 59
<211> LENGTH: 89
<212> TYPE: DNA
<213> ORGANISM: Artificial Sequence
<220> FEATURE:
<223> OTHER INFORMATION: vioD_T2A7_rev

<400> SEQUENCE: 59
tgggccggga ttctcctcta catcaccaca agtcaacagt gatcctctgc cttctgccct        60
tctttgcaag gcgtatctaa ggttttgtg                                           89

<210> SEQ ID NO 60
<211> LENGTH: 88
<212> TYPE: DNA
<213> ORGANISM: Artificial Sequence
<220> FEATURE:
<223> OTHER INFORMATION: T2A7_vioA_fw

<400> SEQUENCE: 60
agggcagaag gcagaggatc tctgttgact tgtggtgatg tagaggagaa tcccggccca        60
aaacactctt ccgacatttg tattgtcg                                            88

<210> SEQ ID NO 61
<211> LENGTH: 67
<212> TYPE: DNA
<213> ORGANISM: Artificial Sequence
<220> FEATURE:
<223> OTHER INFORMATION: vioA_AOX_TT_rev

<400> SEQUENCE: 61
caggcaaatg gcattctgac atcctcttga gcggccgctt aggcagcaat tctttgcaaa        60
agcaaac                                                                   67

<210> SEQ ID NO 62
<211> LENGTH: 85
<212> TYPE: DNA
<213> ORGANISM: Artificial Sequence
<220> FEATURE:
<223> OTHER INFORMATION: crtY_T2A8_rev

<400> SEQUENCE: 62
agggcctggg ttctcttcca catctccaca agttaaaaga gagcctctcc cctccgccct        60
acgatgagtc gtcataatgg cttgc                                               85

<210> SEQ ID NO 63
<211> LENGTH: 86
<212> TYPE: DNA
<213> ORGANISM: Artificial Sequence
<220> FEATURE:
<223> OTHER INFORMATION: T2A8_ vioC_fw

<400> SEQUENCE: 63
agggcggagg ggagaggctc tcttttaact tgtggagatg tggaagagaa cccaggccct        60
aagagagcta tcattgttgg tggagg                                              86

<210> SEQ ID NO 64
<211> LENGTH: 85
<212> TYPE: DNA
<213> ORGANISM: Artificial Sequence
<220> FEATURE:
<223> OTHER INFORMATION: T2A_crtE_fw -continued

<400> SEQUENCE: 64
agagctgagg gtagaggttc tttgcttact tgcggtgacg ttgaggaaaa cccaggtcca    60
gaattccgaa acgatgacgg tctgc    85

<210> SEQ ID NO 65
<211> LENGTH: 81
<212> TYPE: DNA
<213> ORGANISM: Artificial Sequence
<220> FEATURE:
<223> OTHER INFORMATION: crtB_T2A_rev

<400> SEQUENCE: 65
tggacctggg ttttcctcaa cgtcaccgca agtaagcaaa gaacctctac cctcagctct    60
gagcgggcgc tgccagagat g    81

<210> SEQ ID NO 66
<211> LENGTH: 86
<212> TYPE: DNA
<213> ORGANISM: Artificial Sequence
<220> FEATURE:
<223> OTHER INFORMATION: T2A_crtI_fw

<400> SEQUENCE: 66
agagctgagg gtagaggttc tttgcttact tgcggtgacg ttgaggaaaa cccaggtcca    60
aaaccaacta cggtaattgg tgcagg    86

<210> SEQ ID NO 67
<211> LENGTH: 87
<212> TYPE: DNA
<213> ORGANISM: Artificial Sequence
<220> FEATURE:
<223> OTHER INFORMATION: crtI_T2A_rev

<400> SEQUENCE: 67
tggacctggg ttttcctcaa cgtcaccgca agtaagcaaa gaacctctac cctcagctct    60
tatcagatcc tccagcatca aacctgc    87

<210> SEQ ID NO 68
<211> LENGTH: 88
<212> TYPE: DNA
<213> ORGANISM: Artificial Sequence
<220> FEATURE:
<223> OTHER INFORMATION: T2A_crtY_fw

<400> SEQUENCE: 68
agagctgagg gtagaggttc tttgcttact tgcggtgacg ttgaggaaaa cccaggtcca    60
caaccgcatt atgatctgat tctcgtgg    88

<210> SEQ ID NO 69
<211> LENGTH: 82
<212> TYPE: DNA
<213> ORGANISM: Artificial Sequence
<220> FEATURE:
<223> OTHER INFORMATION: crtY_T2A_rev

<400> SEQUENCE: 69
tggacctggg ttttcctcaa cgtcaccgca agtaagcaaa gaacctctac cctcagctct    60
gcggccgctt aacgatgagt cg    82

<210> SEQ ID NO 70
<211> LENGTH: 82

<212> TYPE: DNA
<213> ORGANISM: Artificial Sequence
<220> FEATURE:
<223> OTHER INFORMATION: pGAP_vioA_fw

<400> SEQUENCE: 70 gtccctatttt caatcaattg aacaactatc aaaacacaga attccgaaac gatgaaacac    60
tcttccgaca tttgtattgt cg    82

<210> SEQ ID NO 71
<211> LENGTH: 84
<212> TYPE: DNA
<213> ORGANISM: Artificial Sequence
<220> FEATURE:
<223> OTHER INFORMATION: pAOX_vioA_fw

<400> SEQUENCE: 71
cgacaacttg agaagatcaa aaacaacta attattgaaa gaattccgaa acgatgaaac    60
actcttccga catttgtatt gtcg    84

<210> SEQ ID NO 72
<211> LENGTH: 88
<212> TYPE: DNA
<213> ORGANISM: Artificial Sequence
<220> FEATURE:
<223> OTHER INFORMATION: vioC_opt_T2A8_rev

<400> SEQUENCE: 72
agggcctggg ttctcttcca catctccaca agttaaaaga gagcctctcc cctccgccct    60
gttaactcta ccaatcttgt accagacg    88

<210> SEQ ID NO 73
<211> LENGTH: 82
<212> TYPE: DNA
<213> ORGANISM: Artificial Sequence
<220> FEATURE:
<223> OTHER INFORMATION: T2A8_crtE_fw

<400> SEQUENCE: 73
agggcggagg ggagaggctc tcttttaact tgtggagatg tggaagagaa cccaggccct    60
acggtctgcg caaaaaaaca cg    82

<210> SEQ ID NO 74
<211> LENGTH: 52
<212> TYPE: DNA
<213> ORGANISM: Artificial Sequence
<220> FEATURE:
<223> OTHER INFORMATION: crtY_AOX_TT_rev

<400> SEQUENCE: 74
caggcaaatg gcattctgac atcctcttga gcggccgctt aacgatgagt cg    52

<210> SEQ ID NO 75
<211> LENGTH: 66
<212> TYPE: DNA
<213> ORGANISM: Artificial Sequence
<220> FEATURE:
<223> OTHER INFORMATION: DAS1TT_vioA_fw

<400> SEQUENCE: 75
ctcctaacta aaactgtaaa gacttcccgt actagtttag gcagcaattc tttgcaaaag    60
caaacg    66

<210> SEQ ID NO 76
<211> LENGTH: 75
<212> TYPE: DNA
<213> ORGANISM: Artificial Sequence
<220> FEATURE:
<223> OTHER INFORMATION: HTX1_vioB_rev

<400> SEQUENCE: 76
gaaagtggat tcttgggaag tccaaaatag acattttgat ttgtttaggt aacttgaact    60
ggatgtatta gtttg    75

<210> SEQ ID NO 77
<211> LENGTH: 65
<212> TYPE: DNA
<213> ORGANISM: Artificial Sequence
<220> FEATURE:
<223> OTHER INFORMATION: vioB_TBF4_fw_new

<400> SEQUENCE: 77
gtggaaagtt atctcgtgaa gcttaagtac gtagtttcgc ttagtttaag actaaactaa    60
tgttg    65

<210> SEQ ID NO 78
<211> LENGTH: 62
<212> TYPE: DNA
<213> ORGANISM: Artificial Sequence
<220> FEATURE:
<223> OTHER INFORMATION: TBF4_vioE_rev_new

<400> SEQUENCE: 78
cgctgtcttc gccgctaaga gataagccga atagtttgta tacgtcttat gtaatgagtt    60
tc    62

<210> SEQ ID NO 79
<211> LENGTH: 71
<212> TYPE: DNA
<213> ORGANISM: Artificial Sequence
<220> FEATURE:
<223> OTHER INFORMATION: vioE_HHX1_fw

<400> SEQUENCE: 79
gcaaaggtgg ctcacggttt tccattttc tttacctgga tataaataaa aaaaggaaa    60 cacaatctct g    71

<210> SEQ ID NO 80
<211> LENGTH: 70
<212> TYPE: DNA
<213> ORGANISM: Artificial Sequence
<220> FEATURE:
<223> OTHER INFORMATION: HHX1_vioD_rev

<400> SEQUENCE: 80
cctgcaccaa tcacaaggat cttcatgttt tatcgatagt agttgagcaa taaaaaaaag    60
gagaaaaagc    70

<210> SEQ ID NO 81
<211> LENGTH: 53
<212> TYPE: DNA
<213> ORGANISM: Artificial Sequence
<220> FEATURE:
<223> OTHER INFORMATION: vioD_DAS2TT_fw

<400> SEQUENCE: 81
ccttagatac gccttgcaaa gataagtaga tttggccact aacgggttag tag        53

<210> SEQ ID NO 82
<211> LENGTH: 48
<212> TYPE: DNA
<213> ORGANISM: Artificial Sequence
<220> FEATURE:
<223> OTHER INFORMATION: DAS2TT_GAP_rev

<400> SEQUENCE: 82
ggacaccaag acatttctac aaaaagacgg ggttcgtaaa ctggttcc              48

<210> SEQ ID NO 83
<211> LENGTH: 56
<212> TYPE: DNA
<213> ORGANISM: Artificial Sequence
<220> FEATURE:
<223> OTHER INFORMATION: DAS2TT_GAP_fw

<400> SEQUENCE: 83
gaggaaccag tttacgaacc ccgtcttttt gtagaaatgt cttggtgtcc tcgtcc     56

<210> SEQ ID NO 84
<211> LENGTH: 63
<212> TYPE: DNA
<213> ORGANISM: Artificial Sequence
<220> FEATURE:
<223> OTHER INFORMATION: GAP_vioC_rev

<400> SEQUENCE: 84
caccaacaat gatagctctc ttcattgtgt tttgatagtt gttcaattga ttgaaatagg  60
gac                                                               63

<210> SEQ ID NO 85
<211> LENGTH: 71
<212> TYPE: DNA
<213> ORGANISM: Artificial Sequence
<220> FEATURE:
<223> OTHER INFORMATION: BZ6_vioB_rev

<400> SEQUENCE: 85
gattcttggg aagtccaaaa tagacatttt tgatgtttga tagtttgata agagtgaact  60
ttagtgttta g                                                      71

<210> SEQ ID NO 86
<211> LENGTH: 61
<212> TYPE: DNA
<213> ORGANISM: Artificial Sequence
<220> FEATURE:
<223> OTHER INFORMATION: vioE_BZF8_fw

<400> SEQUENCE: 86
gcaaaggtgg ctcacggttt tccatcttag attttttttt ttgcttggtg ggattccttc  60
g                                                                 61

<210> SEQ ID NO 87
<211> LENGTH: 62
<212> TYPE: DNA
<213> ORGANISM: Artificial Sequence
<220> FEATURE:
<223> OTHER INFORMATION: BZF8_vioD_rev

<400> SEQUENCE: 87

```
ctgcaccaat cacaaggatc ttcattgtga atatcaagaa ttgtatgaac aagcaaagtt    60
gg                                                                   62
```

```
<210> SEQ ID NO 88
<211> LENGTH: 53
<212> TYPE: DNA
<213> ORGANISM: Artificial Sequence
<220> FEATURE:
<223> OTHER INFORMATION: DAS2TT_FDH1_fw

<400> SEQUENCE: 88
ggaaccagtt tacgaaccccc gtctgggtgc ggaaccagct tctaattaaa tag           53
```

```
<210> SEQ ID NO 89
<211> LENGTH: 55
<212> TYPE: DNA
<213> ORGANISM: Artificial Sequence
<220> FEATURE:
<223> OTHER INFORMATION: FDH1_vioC_rev

<400> SEQUENCE: 89
caccaacaat gatagctctc ttcattgttt aagtgggtga tgttggaggt atttg          55
```

```
<210> SEQ ID NO 90
<211> LENGTH: 65
<212> TYPE: DNA
<213> ORGANISM: Artificial Sequence
<220> FEATURE:
<223> OTHER INFORMATION: vioB_TBF4_fw_new

<400> SEQUENCE: 90
gtggaaagtt atctcgtgaa gcttaagtac gtagtttcgc ttagtttaag actaaactaa    60
tgttg                                                                65
```

```
<210> SEQ ID NO 91
<211> LENGTH: 62
<212> TYPE: DNA
<213> ORGANISM: Artificial Sequence
<220> FEATURE:
<223> OTHER INFORMATION: TBF4_vioE_rev_new

<400> SEQUENCE: 91
cgctgtcttc gccgctaaga gataagccga atagtttgta tacgtcttat gtaatgagtt    60
tc                                                                   62
```

```
<210> SEQ ID NO 92
<211> LENGTH: 29
<212> TYPE: DNA
<213> ORGANISM: Artificial Sequence
<220> FEATURE:
<223> OTHER INFORMATION: T2A_Ubiqitin_GFP_fw

<400> SEQUENCE: 92
agagctgagg gtagaggttc tttgcttac                                      29
```

```
<210> SEQ ID NO 93
<211> LENGTH: 29
<212> TYPE: DNA
<213> ORGANISM: Artificial Sequence
<220> FEATURE:
<223> OTHER INFORMATION: T2A_Ubiqitin_GFP_rev

<400> SEQUENCE: 93
gggacaactc cagtgaaaag ttcttctcc                                      29
```

<210> SEQ ID NO 94
<211> LENGTH: 59
<212> TYPE: DNA
<213> ORGANISM: Artificial Sequence
<220> FEATURE:
<223> OTHER INFORMATION: Ubiquitin_GFP_fw

<400> SEQUENCE: 94
gcacttggtc cttagactta gaggaggtat ggctagcaaa ggagaagaac ttttcactg    59

<210> SEQ ID NO 95
<211> LENGTH: 56
<212> TYPE: DNA
<213> ORGANISM: Artificial Sequence
<220> FEATURE:
<223> OTHER INFORMATION: Ubiquitin_GFPohne_fw

<400> SEQUENCE: 95
gcacttggtc cttagactta gaggaggtgc tagcaaagga gaagaacttt tcactg    56

<210> SEQ ID NO 96
<211> LENGTH: 56
<212> TYPE: DNA
<213> ORGANISM: Artificial Sequence
<220> FEATURE:
<223> OTHER INFORMATION: Ubiquitin_GFPohne_rev

<400> SEQUENCE: 96
cagtgaaaag ttcttctcct tgctagcac ctcctctaag tctaaggacc aagtgc    56

<210> SEQ ID NO 97
<211> LENGTH: 77
<212> TYPE: DNA
<213> ORGANISM: Artificial Sequence
<220> FEATURE:
<223> OTHER INFORMATION: eGFP_Gibson_rev

<400> SEQUENCE: 97
ctctcaggca aatggcattc tgacatcctc ttgagcggcc gcttacttgt acaattcatc    60
catgccatgt gtaatcc    77

<210> SEQ ID NO 98
<211> LENGTH: 105
<212> TYPE: DNA
<213> ORGANISM: Artificial Sequence
<220> FEATURE:
<223> OTHER INFORMATION: sTomato_AOX_Gibson_His_fwd

<400> SEQUENCE: 98
acgacaactt gagaagatca aaaacaact aattattgaa agaattccga aacgatgcac    60
caccatcacc accatgtttc taagggtgag gaagttatca aggag    105

<210> SEQ ID NO 99
<211> LENGTH: 94
<212> TYPE: DNA
<213> ORGANISM: Artificial Sequence
<220> FEATURE:
<223> OTHER INFORMATION: sTomato_T2A_rev

<400> SEQUENCE: 99
tggacctggg ttttcctcaa cgtcaccgca agtaagcaaa gaacctctac cctcagctct    60
cttataaagc tcgtccatac cgtacaagaa caag    94